US012629537B2

(12) United States Patent
Do et al.

(10) Patent No.: US 12,629,537 B2
(45) Date of Patent: May 19, 2026

(54) FLEXIBLE ULTRA-THIN LED SKIN PATCH AND MANUFACTURING METHOD THEREOF

(71) Applicant: KOOKMIN UNIVERSITY INDUSTRY ACADEMY COOPERATION FOUNDATION, Seoul (KR)

(72) Inventors: Young Rag Do, Seoul (KR); Min Ji Ko, Seoul (KR)

(73) Assignee: KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 838 days.

(21) Appl. No.: 17/879,731

(22) Filed: Aug. 2, 2022

(65) Prior Publication Data

US 2023/0114186 A1     Apr. 13, 2023

(30) Foreign Application Priority Data

Aug. 2, 2021     (KR) ......................... 10-2021-0101273

(51) Int. Cl.
*A61N 5/06*          (2006.01)
*H10H 20/01*        (2025.01)
(Continued)

(52) U.S. Cl.
CPC ..... *A61N 5/0616* (2013.01); *H10H 20/01335* (2025.01); *H10H 20/018* (2025.01);
(Continued)

(58) Field of Classification Search
CPC .......... A61N 5/0616; A61N 2005/0651; A61N 2005/0661; A61N 2005/0645;
(Continued)

(56) References Cited

U.S. PATENT DOCUMENTS

2004/0116913 A1*   6/2004   Pilcher ................. A61N 5/0616
                                                                  606/9
2006/0271132 A1*  11/2006   Fiset ...................... B82Y 20/00
                                                                  607/94
(Continued)

FOREIGN PATENT DOCUMENTS

KR          2006-0105396 A      10/2006
KR             10-1490758 B1     2/2015
(Continued)

OTHER PUBLICATIONS

Manager, "What is a micro LED display?", 7 pages, May 11, 2018. Retrieved on Jun. 2, 2023, from http://hidisplay.co.kr/FAQ/1712531.
(Continued)

*Primary Examiner* — William J Levicky
*Assistant Examiner* — Rumaisa Rashid Baig
(74) *Attorney, Agent, or Firm* — Foley & Lardner LLP

(57)          ABSTRACT
The present invention relates to a flexible skin patch equipped with an ultra-thin LED assembly that emits light in a specific wavelength range and an invention for manufacturing the same, and is related to an invention capable of providing a flexible skin patch that has the excellent effect of promoting vitamin D production in a localized area of the skin, and has the effect of alleviating or treating local skin psoriasis, fungi, fungal tumors and eczema, and has excellent antiviral effect, and is easy to attach and detach.

19 Claims, 20 Drawing Sheets

1000

(51) Int. Cl.

| | |
|---|---|
| *H10H 20/813* | (2025.01) |
| *H10H 20/816* | (2025.01) |
| *H10H 20/821* | (2025.01) |
| *H10H 20/825* | (2025.01) |
| *H10H 20/831* | (2025.01) |
| *H10H 20/852* | (2025.01) |

(52) U.S. Cl.
CPC ........ *H10H 20/813* (2025.01); *H10H 20/816* (2025.01); *H10H 20/821* (2025.01); *H10H 20/825* (2025.01); *H10H 20/8316* (2025.01); *H10H 20/852* (2025.01); *A61N 2005/0651* (2013.01); *A61N 2005/0661* (2013.01); *H10H 20/032* (2025.01)

(58) Field of Classification Search
CPC .......... A61N 5/0624; A61N 2005/0643; A61N 2005/0652; H10H 20/01335; H10H 20/018; H10H 20/813; H10H 20/816; H10H 20/821; H10H 20/825; H10H 20/8316; H10H 20/852; H10H 20/032; H10H 20/034; H10H 20/819; H10H 20/01; H10H 20/84; H10H 20/83

See application file for complete search history.

(56) References Cited

U.S. PATENT DOCUMENTS

| | | | | |
|---|---|---|---|---|
| 2007/0156124 A1* | 7/2007 | Ignon | ................... | A61M 1/962 606/9 |
| 2007/0276455 A1* | 11/2007 | Fiset | ...................... | B82Y 30/00 607/91 |
| 2008/0172113 A1* | 7/2008 | Gourgouliatos | ..... | A61N 5/0617 607/90 |
| 2008/0258160 A1* | 10/2008 | Do | ..................... | H10H 20/8516 257/E33.068 |
| 2008/0269849 A1* | 10/2008 | Lewis | ................... | A61N 5/0613 607/91 |
| 2009/0177125 A1* | 7/2009 | Pilcher | .................. | A61H 7/005 15/4 |
| 2009/0177256 A1* | 7/2009 | Ripper | ................. | A61N 5/0616 607/90 |
| 2012/0160157 A1* | 6/2012 | Han | .................. | H01L 21/02579 117/109 |
| 2012/0263793 A1* | 10/2012 | Vitaliano | ............. | G01N 21/648 424/490 |
| 2012/0286296 A1* | 11/2012 | So | .......................... | H10K 65/00 257/E51.012 |
| 2013/0087821 A1* | 4/2013 | Do | ..................... | H10H 20/8515 257/98 |
| 2013/0345620 A1* | 12/2013 | Zemel | ................. | H05H 1/2418 604/24 |
| 2016/0148911 A1* | 5/2016 | Do | ......................... | H05K 1/111 438/28 |
| 2017/0138549 A1* | 5/2017 | Do | ...................... | H10H 20/818 |
| 2019/0116658 A1* | 4/2019 | Jeong | .................... | C09J 125/08 |
| 2020/0188660 A1* | 6/2020 | Franke | .............. | A61N 1/36071 |
| 2020/0335590 A1* | 10/2020 | Nidhi | .................. | H10D 64/662 |
| 2021/0167050 A1* | 6/2021 | Cho | ................... | H01L 25/0753 |

FOREIGN PATENT DOCUMENTS

| | | |
|---|---|---|
| KR | 2015-0021613 A | 3/2015 |
| KR | 10-1627365 B1 | 6/2016 |
| KR | 2017-0072553 A | 6/2017 |
| KR | 2018-0095471 A | 8/2018 |
| KR | 2019-0024615 A | 3/2019 |
| KR | 2019-0117413 A | 10/2019 |
| KR | 10-2020-0021014 A | 2/2020 |
| KR | 2020-0011302 A | 2/2020 |

OTHER PUBLICATIONS

Office Action from Korean Application No. 10-2021-0101273, May 19, 2023, 8 pages.

* cited by examiner

X-X'

102

103

1001

301
300
302

100
500
101
301
600
400
211   212   213   214
200

X-X'

107

X-X'

Y-Y'

FLEXIBLE ULTRA-THIN LED SKIN PATCH AND MANUFACTURING METHOD THEREOF

CROSS REFERENCE TO RELATED APPLICATION

The present application claims priority to Korean Patent Application No. 10-2021-0101273, filed Aug. 2, 2021, the entire contents of which is incorporated herein for all purposes by this reference.

BACKGROUND OF THE INVENTION

Field of the Invention

The present invention relates to a flexible skin patch equipped with an LED that is attached to the skin and emits light in a specific wavelength range, and more particularly, to a flexible skin patch equipped with an ultra-thin LED assembly and an invention for manufacturing the same.

Description of the Related Art

Recently, skin beauty and skin treatment using light are being actively used, and since each cell and tissue of the skin absorbs light of a specific wavelength, for the purpose of physiological and chemical treatments, the skin is irradiated with light in the appropriate wavelength range to induce a skin reaction.

Light treatment for skin disease treatment and skin care is made through light irradiation using lasers, lamps, or LEDs, and recently, various small cosmetic devices and medical devices for simple skin care and/or skin disease treatment at home as well as in medical institutions such as hospitals have been developed and marketed.

The types of LEDs currently developed are very diverse. In particular, among various LEDs, micro LED and nano LED can realize excellent color and high efficiency, and are eco-friendly materials, so they are used as core materials for various light sources and displays. In line with these market conditions, research to develop a new nanorod LED structure or a shell-coated nanocable LED by a new manufacturing process is in progress. In addition, research on a protective film material to achieve high efficiency and high stability of a protective film covering the outer surface of the nanorod, or research on a ligand material advantageous for the subsequent process is in progress.

In line with such research in the field of materials, display TVs using red, green, and blue micro-LEDs have recently been commercialized. Display and various light sources using micro-LED have high performance characteristics, theoretically very long lifespan and high efficiency. However, micro LEDs must be individually placed on miniaturized electrodes in a limited area. Accordingly, considering high unit cost, high defect rate in manufacturing process, and low productivity, the electrode assembly implemented by placing micro-LEDs on electrodes with pick place technology is difficult to manufacture as a true high-resolution commercial display from smartphones to TVs or light sources with various sizes, shapes, and brightness due to the limitations of process technology. In addition, it is more difficult to individually arrange nano-LEDs, which are smaller than micro-LEDs, on the electrodes with the same pick and place technology as in the case of micro-LEDs.

In order to overcome these difficulties, KR Patent Registration No. 10-1490758 by the present inventor discloses an ultra-thin LED electrode assembly manufactured through a method of self-aligning nanorod-type LED devices on an electrode by dropping a solution in which nanorod-type LEDs are mixed on the electrode and forming an electric field between two different electrodes.

However, in the disclosed technology, as the LED devices are aligned through an electric field, the LED devices must have a rod shape with a large aspect ratio, which is formed elongated in one direction. As such, the rod-type LED devices with a large aspect ratio are easily precipitated in a solvent, making it difficult to ink the LED devices, and thus, it is not easy to implement a large-area electrode assembly through inkjet printing.

In addition, as the devices are assembled by laying on two different electrodes, that is, the stacking direction of each semiconductor layer in the devices and the main surfaces of the electrodes are assembled in parallel, the area from which light is extracted is small, so there is a problem in that the efficiency is not good. Specifically, nanorod-type LED devices are known to be manufactured by a top-down method in which the nanopatterning process and dry etching/wet etching are mixed on an LED wafer, or grow directly on a substrate by a bottom-up method. In these nanorod-type LEDs, the long axis of the LED coincides with a stacking direction, that is, the stacking direction of each layer in the Stacked structure of p-GaN/InGaN multiple quantum well (MQW)/n-GaN, p-GaN/InGaN multiple quantum well (MQW)/n-GaN/InGaN. Thus, an emitting area is narrow, and because the emitting area is narrow, surface defects have a relatively large influence on the decrease in efficiency. In addition, it is difficult to optimize a recombination rate of electron-hole, so there is a problem that emission efficiency is significantly lower than that of an original wafer.

Furthermore, since two different electrodes formed in order to emit light of the nanorod-type LED device must be formed on the same plane, there is a problem in that electrode design is not easy.

DOCUMENTS OF RELATED ART (Patent Document 1) KR Patent Registration No. 10-1490758 (published date Mar. 26, 2019)

SUMMARY OF THE INVENTION

The inventor of the present invention has developed a new ultra-thin LED assembly that solves the problems of the existing nanorod-type LED. The ultra-thin LED assembly of the present invention is to be used as a display device, a lighting device, as well as a cosmetic device for skin improvement or a medical device for treating or alleviating skin disease. The present invention is to provide a flexible ultra-thin LED skin patch that is directly attached to the skin as a flexible skin patch equipped with the ultra-thin LED assembly and can improve skin conditions and alleviate or treat skin diseases by emitting light of a specific wavelength, and a manufacturing method thereof.

In order to achieve the above objects, a flexible ultra-thin LED skin patch of the present invention includes an LED electrode assembly including an ultra-thin LED device in which a first conductive semiconductor layer, a photoactive layer, and a second conductive semiconductor layer are stacked, the ultra-thin LED device includes an LED device that emits UV of a wavelength of 200 to 400 nm.

In a preferred embodiment of the present invention, the ultra-thin LED device may include at least one selected from the LED device emitting UVC of the wavelength of 200 to 280 nm, the LED device emitting UVB of the wavelength of 280 to 320 nm, and the LED device emitting UVA of the wavelength of 221 to 400 nm.

In a preferred embodiment of the present invention, the ultra-thin LED device includes at least one selected from a dot type LED device, a disk type LED device, and a micro-nanofin LED device. In the dot type and disk type LED devices, a thickness in a stacking direction of the layers is 2,000 nm or less, the dot type LED device has a ratio between the thickness and a length of a long axis in a cross-section perpendicular to the stacking direction of 1:0.5 to 1.5, the disc type LED device has the ratio of 1:1.5 to 5.0. In the micro-nanofin LED device, the thickness in the stacking direction is 100 to 3,000 nm and a length of the long axis in the vertical cross-section is 100 to 10,000 nm, and the micro-nanofin LED device has the ratio between the thickness and the length of the long axis of 1:3.

In a preferred embodiment of the present invention, the LED electrode assembly includes a lower electrode line including a single or a plurality of lower electrodes; a plurality of the ultra-thin LED devices that is erected and disposed on the lower electrode in the stacking direction of the layers; and an upper electrode line including a single or a plurality of upper electrodes disposed on the plurality of ultra-thin LED devices.

In a preferred embodiment of the present invention, the ultra-thin LED device may further include an arrangement inducing layer that erects and disposes the ultra-thin LED device in a thickness direction on one side of the ultra-thin LED device in the thickness direction and either one or both sides of a disposing area in which the ultra-thin LED device is to be disposed.

In a preferred embodiment, the arrangement inducing layer may be a magnetic layer, a charge layer or a binding layer.

In a preferred embodiment, the ultra-thin LED device may have a maximum surface area of 16 μm² or less.

In a preferred embodiment of the present invention, the first conductive semiconductor layer of the ultra-thin LED device is an n-type III-nitride semiconductor layer, and an electron delay layer on a surface opposite to one surface of the first conductive semiconductor layer adjacent to the photoactive layer so that a number of recombination electrons and a number of recombination holes in the photoactive layer are balanced may be further included.

In a preferred embodiment of the present invention, the electron delay layer may be a III-nitride semiconductor having a doping concentration lower than that of the first conductive semiconductor layer.

In a preferred embodiment of the present invention, the second conductive semiconductor layer of the ultra-thin LED device is a p-type III-nitride semiconductor layer, and an electron delay layer on a surface opposite to one surface of the second conductive semiconductor layer adjacent to the photoactive layer so that a number of recombination electrons and a number of recombination holes in the photoactive layer are balanced may be further included.

In a preferred embodiment of the present invention, the electron delay layer may include at least one selected from CdS, GaS, ZnS, CdSe, CaSe, ZnSe, CdTe, GaTe, SiC, ZnO, ZnMgO, SnO₂, TiO₂, In₂O₃, Ga₂O₃, Si, poly(para-phenylene vinylene) and derivatives thereof, polyaniline, poly (3-alkylthiophene) and poly(paraphenylene).

In a preferred embodiment of the present invention, in the ultra-thin LED device, the first conductive semiconductor layer is an n-type III-nitride semiconductor layer, and the second conductive semiconductor layer is a p-type III-nitride semiconductor layer. The ultra-thin LED device may further include at least one film of a hole pushing film that surrounds an exposed side surface of the second conductive semiconductor layer or the exposed side surface of the second conductive semiconductor layer and an exposed side surface of at least a portion of the photoactive layer to move a hole on the exposed side surface toward a center; and an electron pushing film that surrounds an exposed side surface of the first conductive semiconductor layer to move an electron on the exposed side surface toward the center.

In a preferred embodiment of the present invention, the ultra-thin LED device includes both the hole pushing film and the electron pushing film, and the electron pushing film may be provided as an outermost film surrounding the side surfaces of the first conductive semiconductor layer, photoactive layer, and second conductive semiconductor layer.

In a preferred embodiment of the present invention, the hole pushing film may include at least one selected from AlN_X, ZrO₂, MoO, Sc₂O₃, La₂O₃, MgO, Y₂O₃, Al₂O₃, Ga₂O₃, TiO₂, ZnS, Ta₂O₅ and n-MoS₂.

In a preferred embodiment of the present invention, the electron pushing film may include at least one selected from Al₂O₃, HfO₂, SiN_x, SiO₂, ZrO₂, Sc₂O₃, AlN_x and Ga₂O₃.

In a preferred embodiment of the present invention, when the ultra-thin LED device is the micro-nanofin LED device, the micro-nanofin LED device may further include a polarization inducing layer stacked on an upper portion of the second conductive semiconductor layer.

In a preferred embodiment of the present invention, when the ultra-thin LED device is the micro-nanofin LED device, the first conductive semiconductor layer or polarization inducing layer of the micro-nanofin LED device is disposed so as to be in contact with at least two adjacent lower electrodes.

In a preferred embodiment of the present invention, the polarization inducing layer may be configured such that electrical polarities of both ends of the device in the longitudinal direction may be different from each other.

In a preferred embodiment of the present invention, the polarization inducing layer includes a first polarization inducing layer and a second polarization inducing layer disposed adjacent to each other in the longitudinal direction of the device, and the first polarization inducing layer and the second polarization inducing layer may have different electrical polarities. In this case, for example, the first polarization inducing layer may be ITO, and the second polarization inducing layer may be a metal, a dielectric, or a semiconductor.

In a preferred embodiment of the present invention, the length may be 100 to 5000 nm and the thickness may be 100 to 3000 nm.

In a preferred embodiment of the present invention, the ratio of the length and the thickness of the micro-nanofin LED device may be 3:1 or more.

In a preferred embodiment of the present invention, a protrusion having a predetermined width and thickness may be formed on the lower surface of the first conductive semiconductor layer of the micro-nanofin LED device in the longitudinal direction of the device.

In a preferred embodiment of the present invention, the width of the protrusion may be formed to have a length of 50% or less compared to the width of the micro-nanofin LED device.

In a preferred embodiment of the present invention, the emitting area of the micro-nanofin LED device may exceed twice the longitudinal cross sectional area of the micro-nanofin LED device.

In a preferred embodiment of the present invention, the LED electrode assembly may be formed on a flexible substrate.

In a preferred embodiment of the present invention, a substrate including a skin adhesive layer including an adhesive pad or an adhesive film; and the LED electrode assembly provided on the substrate are included. The substrate and/or the skin adhesive layer may be transparent.

In a preferred embodiment of the present invention, the skin adhesive layer and/or the substrate may have a light transmittance of 70% or more.

In a preferred embodiment of the present invention, the LED electrode assembly is encapsulated with an encapsulant, and each of the lower electrode and the upper electrode may be a flexible electrode.

In a preferred embodiment of the present invention, the flexible skin patch of the present invention may promote a production of vitamin D in a skin.

In a preferred embodiment of the present invention, the flexible skin patch of the present invention may alleviates skin disease or improves skin condition.

Another object of the present invention relates to a method for manufacturing the above-described flexible ultra-thin LED skin patch, which can be manufactured by combining the various LED electrode assembly described above with a substrate including a skin adhesive layer.

In a preferred embodiment of the present invention, when the ultra-thin LED device applied to the LED electrode assembly is a dot type or disk type LED device, the LED electrode assembly may be manufactured by the process including the steps of: (1) preparing a lower electrode line including a lower electrode; (2) processing an ink composition including a plurality of ultra-thin LED devices on the lower electrode; (3) erecting and assembling the ultra-thin LED device in the thickness direction on the lower electrode; (4) filling the periphery of the ultra-thin LED device with an insulator; and (5) forming an upper electrode line including an upper electrode to be electrically connected to the opposite side of the ultra-thin LED device opposite to one side of the ultra-thin LED device assembled to the lower electrode.

In a preferred embodiment of the present invention, a magnetic layer is further provided on one side of the ultra-thin LED device in the thickness direction and on an disposing area within the lower electrode where the ultra-thin LED device is to be disposed. In step 3, a magnetic field may be formed in a direction perpendicular to the main surface of the lower electrode so that the ultra-thin LED device is moved to the disposing area and disposed upright in the thickness direction.

In a preferred embodiment of the present invention, a first charge layer having a positive or negative charge may be further provided on one side of the ultra-thin LED device in the thickness direction, and a second charge layer having a charge opposite to that of the first charge layer may be further provided on a disposing area in the lower electrode where the ultra-thin LED device is to be disposed. In step 3, an electric field may be formed in a direction perpendicular to the main surface of the lower electrode so that the ultra-thin LED device is moved to the disposing area and disposed upright in the thickness direction.

In a preferred embodiment of the present invention, in step 3, the ultra-thin LED device is erected on the disposing area and assembled through chemical bonding via a binding layer between one side of the ultra-thin LED device in the thickness direction and the disposing area in the lower electrode where the ultra-thin LED device is to be disposed, and the binding layer may be provided on one side of the ultra-thin LED device in the thickness direction and either one side or both sides of the disposing area.

In a preferred embodiment of the present invention, when the ultra-thin LED device applied to the LED electrode assembly is a micro-nanofin LED device, the LED electrode assembly is manufactured by a process including the steps of (1) injecting, on a lower electrode line including a plurality of lower electrodes spaced apart in a horizontal direction at a predetermined interval, an ink composition containing a plurality of micro-nanofin LED devices; (2) self-aligning the micro-nanofin LED devices so that the first conductive semiconductor layers or polarization inducing layers of the micro-nanofin LED devices in the solution are in contact with at least two adjacent lower electrodes by applying an assembling voltage to the lower electrode line; and (3) forming an upper electrode line on the plurality of self-aligned micro-nanofin LED devices.

In a preferred embodiment of the present invention, the process may further include, between steps 2 and 3 described above, the steps of (4) forming a conducting metal layer connecting the side surface of the first conductive semiconductor layer or polarization inducing layer of each micro-nanofin LED device in contact with at least two lower electrodes and the at least two lower electrodes, and (5) forming an insulating layer on the lower electrode line such that the upper surfaces of the self-aligned micro-nanofin LED devices are not covered.

Hereinafter, the terms used in the present invention are defined.

In the description of an embodiment according to the present invention, when described as being formed each layer, region, pattern or substrate, or "on", "upper", "top", "under", "lower", or "bottom" of each layer, region, or pattern, the "on", "upper", "top", "under", "lower", or "bottom" has both "directly" and "indirectly" meanings.

BRIEF DESCRIPTION OF THE DRAWINGS

FIG. 1 is a plan view of an ultra-thin LED electrode assembly, and FIG. 2 is a cross-sectional view taken along the line X-X' of FIG. 1.

FIG. 16 is a plan view of a micro-nanofin LED electrode assembly, and FIG. 17 is a cross-sectional view taken along the line X-X' of FIG. 16.

DETAILED DESCRIPTION OF THE INVENTION

Figure 1:
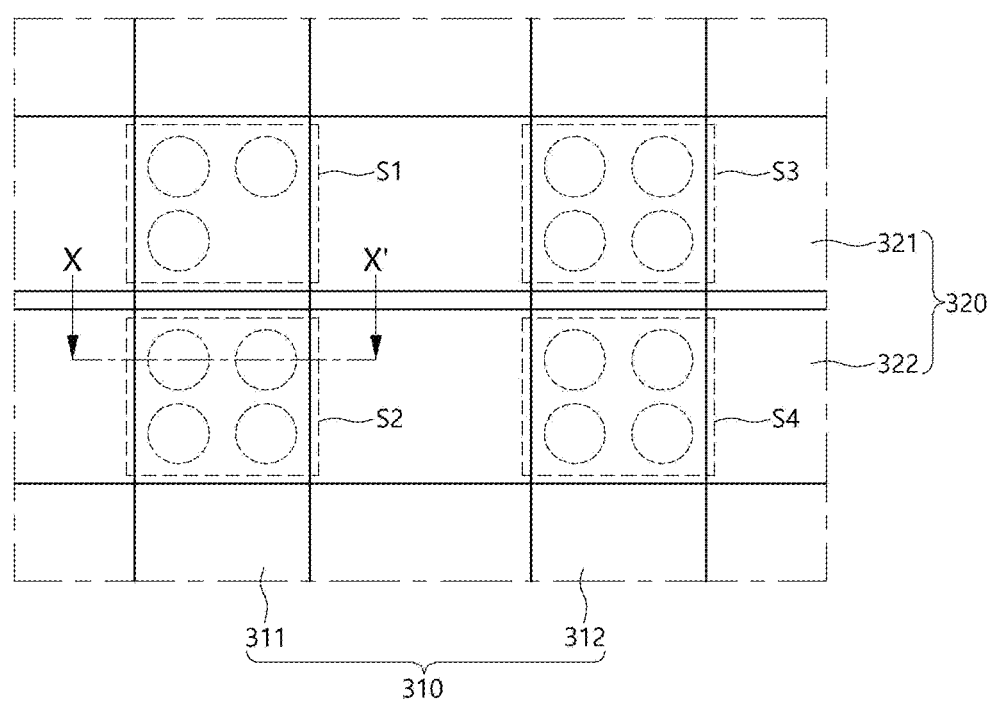
FIGS. 1 and 2 are views of an ultra-thin LED electrode assembly using an ultra-thin LED device (type 1, dot-type, disk-type) according to an embodiment of the present invention.

Hereinafter, the embodiments of the present invention will be described in detail so that those of ordinary skill in the art to which the present invention pertains can easily implement them. The present invention may be embodied in many different forms and is not limited to the embodiments described herein.

A flexible ultra-thin LED skin patch of the present invention includes an LED electrode assembly incorporating an ultra-thin LED device.

An ultra-thin LED device may include an LED device that emits UV of a wavelength of 200 to 400 nm. Preferably, the ultra-thin LED device may include at least one selected from an LED device emitting UVC of a wavelength of 200 to 280 nm, an LED device emitting UVB of a wavelength of 280 to 320 nm, and an LED device emitting UVA of a wavelength of 221 to 400 nm. More preferably, the ultra-thin LED device may include the LED device emitting UVB of a wavelength of 280 to 320 nm.

The LED electrode assembly may be formed (or provided) on a substrate.

The substrate may include a skin adhesive layer including an adhesive pad or an adhesive film. In this case, the adhesive pad is meant to include an adhesive sheet as well.

The substrate may be the skin adhesive layer itself, or may be a transparent adhesive layer formed on one surface of a transparent substrate.

One surface of the skin adhesive layer may further include a protective film (or release film).

The skin adhesive layer and/or substrate is made of a transparent material, and the skin adhesive layer and/or substrate may have a light transmittance of 70% or more, preferably a light transmittance of 80% or more, more preferably a light transmittance of 90 or more.

The substrate is preferably a flexible substrate.

The LED electrode assembly may be implemented to include a lower electrode line including a single or a plurality of lower electrodes; a plurality of ultra-thin LED devices erected and disposed on the lower electrode in a stacking direction of the layers; and an upper electrode line including a single or a plurality of upper electrodes disposed on the plurality of ultra-thin LED devices.

In addition, the lower electrode and the upper electrode may be flexible electrodes.

In addition, the LED electrode assembly may be encapsulated with an encapsulant.

The ultra-thin LED device is an LED device in which a first conductive semiconductor layer, a photoactive layer and a second conductive semiconductor layer are stacked. The ultra-thin LED device may be a dot-type or disk-type LED device (type 1), or a micro-nanofin LED device (type 2).

In the present invention, the ultra-thin LED device may further include an arrangement inducing layer for disposing the ultra-thin LED device upright in one side of a thickness direction and either one or both sides of a disposing area where the ultra-thin LED device is to be disposed in the lower electrode.

In addition, the arrangement inducing layer may be a magnetic layer, a charge layer, or a binding layer.

In addition, the ultra-thin LED device may have a maximum surface area of 16 $\mu m^2$ or less.

The first conductive semiconductor layer of the ultra-thin LED device is an n-type III-nitride semiconductor layer, and may further include an electron delay layer on the surface opposite to one surface of the first conductive semiconductor layer adjacent to the photoactive layer so that the number of recombination electrons and the number of recombination holes in the photoactive layer are balanced.

Also, the electron delay layer may be a III-nitride semiconductor having a lower doping concentration than that of the first conductive semiconductor layer.

In addition, the second conductive semiconductor layer of the ultra-thin LED device is a p-type III-nitride semiconductor layer, and may further include an electron delay layer on the surface opposite to one surface of the second conductive semiconductor layer adjacent to the photoactive layer so that the number of recombination electrons and the number of recombination holes in the photoactive layer are balanced.

In addition, the electron delay layer may include at least one selected from CdS, GaS, ZnS, CdSe, CaSe, ZnSe, CdTe, GaTe, SiC, ZnO, ZnMgO, $SnO_2$, $TiO_2$, $In_2O_3$, $Ga_2O_3$, Si, poly(para-phenylene vinylene) and derivatives thereof, polyaniline, poly(3-alkylthiophene), and poly(paraphenylene).

In addition, in the ultra-thin LED device, the first conductive semiconductor layer is an n-type III-nitride semiconductor layer, and the second conductive semiconductor layer is a p-type III-nitride semiconductor layer. The ultra-thin LED device may further include at least any one of a hole pushing film that surrounds the exposed side surface of the second conductive semiconductor layer or the exposed side surface of the second conductive semiconductor layer and the exposed side surface of at least a portion of the photoactive layer to move holes on the exposed side surface toward the center; and an electron pushing film that surrounds the exposed side surface of the first conductive semiconductor layer to move electrons on the exposed side surface toward the center.

In addition, the ultra-thin LED device may include both the hole pushing film and the electron pushing film, and the electron pushing film may be provided as an outermost film surrounding the side surfaces of the first conductive semiconductor layer, photoactive layer and second conductive semiconductor layer.

In addition, the hole pushing film may include at least one selected from $AlN_x$, $ZrO_2$, $MoO$, $Sc_2O_3$, $La_2O_3$, $MgO$, $Y_2O_3$, $Al_2O_3$, $Ga_2O_3$, $TiO_2$, $ZnS$, $Ta_2O_5$ and $n-MoS_2$.

In addition, the electron pushing film may include at least one selected from $Al_2O_3$, $HfO_2$, $SiN_x$, $SiO_2$, $ZrO_2$, $Sc_2O_3$, $AlN_x$ and $Ga_2O_3$.

For each case of using the first type ultra-thin LED device (dot or disk type ultra-thin LED device) and the second type ultra-thin LED device (micro-nanofin type ultra-thin LED device) for the LED electrode assembly applied to the flexible ultra-thin LED skin patch of the present invention, a preferred embodiment will be described as follows.

[First Type (Dot or Disk) Ultra-Thin LED Electrode Device and LED Electrode Assembly]

An LED electrode assembly manufactured with a first type ultra-thin LED device will be described with reference to FIGS. 1 and 2 as follows.

The ultra-thin LED electrode assembly 1000 according to an embodiment of the present invention is implemented by including a lower electrode line 310 including lower electrodes 311, 312, a plurality of ultra-thin LED devices 101 disposed on the lower electrodes 311, 312, and an upper electrode line 320 including upper electrodes 321, 322 disposed in contact with the upper portion of the ultra-thin LED device 101.

First, before describing each configuration in detail, an electrode line for emitting light from an ultra-thin LED device will be described.

The ultra-thin LED electrode assembly 1000 includes the upper electrode line 320 and the lower electrode line 310 disposed to face the upper and lower portions with the ultra-thin LED devices 101 interposed therebetween. Since the upper electrode line 320 and the lower electrode line 310 are not arranged in a horizontal direction, an electrode design can be very simple and can be implemented more easily by avoiding the complicated electrode line of a conventional electrode assembly in which two types of electrodes implemented to have ultra-thin thickness and width are horizontally disposed to have micro or nano-scale spacing within a plane of a limited area.

Figure 2:
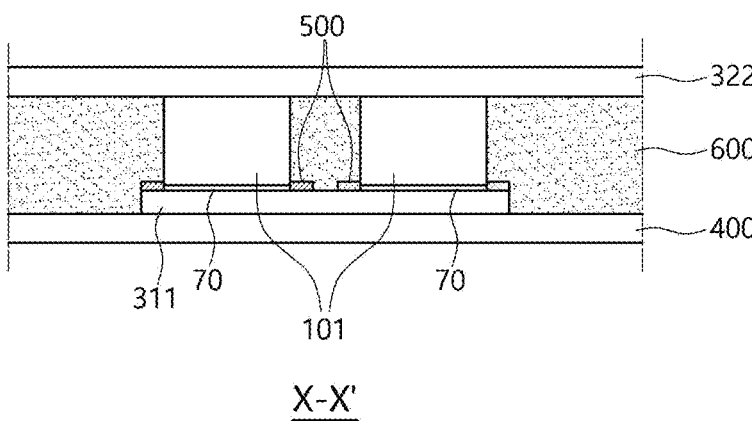

In particular, as shown in FIGS. 1 and 2, regardless of the electrode design of the lower electrode line 310, the upper electrode line 320 is disposed so that electrical contact is possible on the upper surface of the ultra-thin LED device 101 disposed thereon. Therefore, there is an advantage that the design or implementation of the electrode is very easy. In particular, although FIG. 1 shows that the upper electrodes 321, 322 are independent, it can also be implemented to contact the upper surfaces of all ultra-thin LED devices arranged with only one upper electrode, so the electrode line can be very simplified compared to the conventional art.

In addition, the lower electrode line 310 and the upper electrode line 320 may include a plurality of lower electrodes 311, 312 and a plurality of upper electrodes 321, 322, respectively. Since the number, spacing, and disposing shape thereof can be appropriately modified in consideration of the size of the LED electrode assembly to be implemented, the present invention is not particularly limited thereto.

In addition, when the upper electrode line 320 is designed to be in electrical contact with the upper portions of the ultra-thin LED devices 101 mounted on the lower electrode line 310, there is no limitation in the number, disposing shape, or the like. However, as shown in FIG. 1, if the lower electrode lines 310 are arranged side by side in one direction, the upper electrode lines 320 may be arranged to be perpendicular to the one direction, and this electrode disposition is widely used in a commonly employed display and the like. Thus, there is an advantage in that the commonly employed electrode disposition and control technology in a display field can be used as it is.

In addition, the lower electrode line 310 and the upper electrode line 320 may have the material, shape, width, and thickness of an electrode used in a typical LED electrode assembly, and may be manufactured using a known method, so the present invention does not specifically limit the material, shape, width, and thickness of an electrode. For example, the lower electrodes 311, 312 and the upper electrodes 321, 322 may each independently be made of aluminum, chromium, gold, silver, copper, graphene, ITO, AZO, or an alloy thereof, and have a width of 2 to 50 μm, a thickness of 0.1 to 100 μm, but may be appropriately changed in consideration of the size and the like of the desired LED electrode assembly.

According to an embodiment of the present invention, disposing areas $(S_1,S_2,S_3,S_4)$ in which the ultra-thin LED devices 101 are to be disposed may be formed on the lower electrodes 311, 312. The disposing areas $(S_1,S_2,S_3,S_4)$ may be configured in many different ways depending on the purpose, and may be configured to be spaced apart between the disposing areas at a predetermined interval as shown in FIG. 1. Alternatively, unlike in FIG. 1, the entire area on the lower electrodes 311, 312 may be the disposing area.

Next, the ultra-thin LED device 101 disposed between the lower electrode line 310 and the upper electrode line 320 described above will be described.

When described with reference to FIGS. 3 and 4, the ultra-thin LED device 101 according to an embodiment of the present invention includes a first conductive semiconductor layer 10, a photoactive layer 20 and a second conductive semiconductor layer 30. In addition, the ultra-thin LED device 101 may further include an upper electrode layer 60 formed under the first conductive semiconductor layer 10, a lower electrode layer 40 formed on the second conductive semiconductor layer 30, and an arrangement inducing layer 70 formed on the outmost side of the second conductive semiconductor layer 30.

The above-mentioned layers are stacked in any one direction. In the dot type LED, the ratio between a thickness in the stacking direction and a length of a long axis in a cross section perpendicular to the stacking direction may satisfy 1:0.5 to 1.5, preferably 1:0.8 to 1.2, more preferably, 1:0.9 to 1.1.

In addition, in the disk type LED, the ratio between the thickness in the stacking direction and the length of the long axis in the cross section perpendicular to the stacking direction may satisfy 1:1.5 to 5.0, preferably 1:1.5 to 3.0, more preferably 1:1.5 to 2.5. Through this, when the ultra-thin LED device is implemented as inkjet ink, it can exhibit excellent dispersibility in a dispersion medium, and it can be advantageous to maintain a dispersed state without being precipitated for a long time.

In addition, there is no need for a separate additive for maintaining the dispersed state due to the geometrical structure suitable for ink formation, so there is an advantage in that contamination of the lower electrode line 310 or a circuit board due to a separate additive can be prevented in advance. Furthermore, when the ink containing the ultra-thin LED devices is printed on the lower electrode line 310, most of the conventional nanorod-type LED devices with a large aspect ratio are disposed on the electrode while lying down. Thus, it has the advantage that the probability that the ultra-thin LED devices are arranged lying on the electrode is reduced. In addition, when a plurality of devices is assembled on an electrode in a thickness direction, the probability that the plurality of devices is assembled in different directions, in other words, the probability that a p-type conductive semiconductor layer and a n-type conductive semiconductor layer are assembled on the lower electrode in different directions is reduced. Thus, it is possible to reduce the electrical leakage caused by the reverse arrangement, which has the advantage of improving the lifespan. Here, the length of the long axis refers to a diameter when a cross sectional shape is a circle, it refers to a length of the long axis when the cross sectional shape is an ellipse, and it refers to a length of the longest side when the cross sectional shape is a polygonal shape. On the other hand, when the cross section of the ultra-thin LED device is not the same in the thickness direction, the cross section refers to the largest surface of the cross sections.

In addition, the ratio between the length of the short axis and the length of the long axis in the cross section may also satisfy 1:0.5 to 1.5, preferably 1:0.8 to 1.2, more preferably 1:0.9 to 1.1. Through this, it may be more advantageous to achieve the object of the present invention described above. Even if the ratio between the thickness and the length of the long axis is 1:0.5 to 1.5, if the ratio between the lengths of the short axis and long axis in the cross section is out of 1:0.5 to 1.5, it is difficult for the LED device to remain dispersed in the dispersion medium for a long time, so it may be unsuitable for ink formation. In addition, in order to maintain dispersion for a long time in the dispersion medium for the LED device having a geometry unsuitable for such ink formation, an additive must be further contained, and there is a risk of contamination of a driving electrode or circuit board due to the use of the additive. Here, the length of the short axis in the cross section refers to the longest length among the lengths of the axis perpendicular to the long axis.

Figure 3:
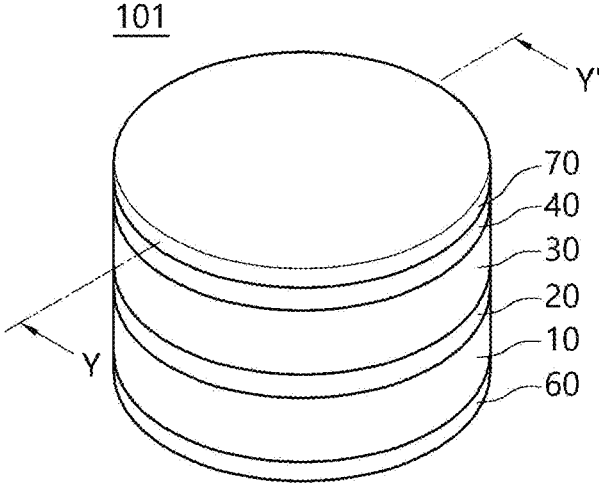
FIG. 3 is a perspective view of an ultra-thin LED device (type 1) used in an embodiment of the present invention.

Meanwhile, although the ultra-thin LED device 101 shown in FIG. 3 has the same size of the cross section perpendicular to the stacking direction of the layers, the size of the cross section is not limited thereto, and the size of the cross section may be different depending on the thickness.

In addition, the shape of the ultra-thin LED device 101 may be a cylinder as shown in FIG. 3, but is not limited thereto. Not only a polyhedron such as a hexahedron, an octahedron, and a decahedron, but also an irregular shape having a star-shaped face may be used.

According to one embodiment of the present invention, the ultra-thin LED device 101 has a maximum surface area of 25 $\mu m^2$ or less, preferably 9 $\mu m^2$ or less, more preferably 4 $\mu m^2$ or less, still more preferably 0.1 to 2.5 $\mu m^2$ as the ultra-thin LED device 101 has excellent dispersion retention performance that can keep the dispersed state due to a slow sedimentation rate during ink formation. Here, the maximum surface area refers to the maximum value among the areas projected by the LED device. If the maximum surface area exceeds 16 $\mu m^2$, the sedimentation rate is high and the dispersion retention performance may be deteriorated, and it may be not suitable to be manufactured as an ink. Also, there may be limitations in further including additional additive or using a specific dispersion medium for ink formation.

According to an embodiment of the present invention, the thickness of the ultra-thin LED device 101 may be 2 $\mu m$ or less, and more preferably 1 $\mu m$ or less. Through this, it may be more suitable for maintaining a dispersed state for a long time during ink formation.

However, in the case of the LED device, if the thickness is thinned, the position where the electrons and the holes are coupled is out of the photoactive layer 20, so that the luminous efficiency may be reduced. In particular, in the case of implementing the ultra-thin LED device by etching a large-area LED wafer, the thicknesses of the first conductive semiconductor layer, photoactive layer, and second conductive semiconductor layer are already determined in the LED wafer, but in spite of this situation, the ultra-thin LED device is implemented by etching only a portion of the wafer to achieve a certain level of luminous efficiency, which is different from the already determined thickness of each layer in the wafer. Accordingly, the above problem inevitably occurs. The change in the position where the electrons and the holes are bounded is due to the difference in the velocities of the electrons and holes moving through the conductive semiconductor layer. For example, in the n-type GaN conductive semiconductor layer, the mobility of electrons is 200 $cm^2/Vs$, whereas in the p-type GaN conductive semiconductor layer, the mobility of holes is only 5 $cm^2/Vs$. Accordingly, due to the electron-hole velocity imbalance, the binding position of electrons and holes is changed according to the thickness of the p-type GaN conductive semiconductor layer and the thickness of the n-type GaN conductive semiconductor layer, and the binding position may leave the photoactive layer.

Figure 6:
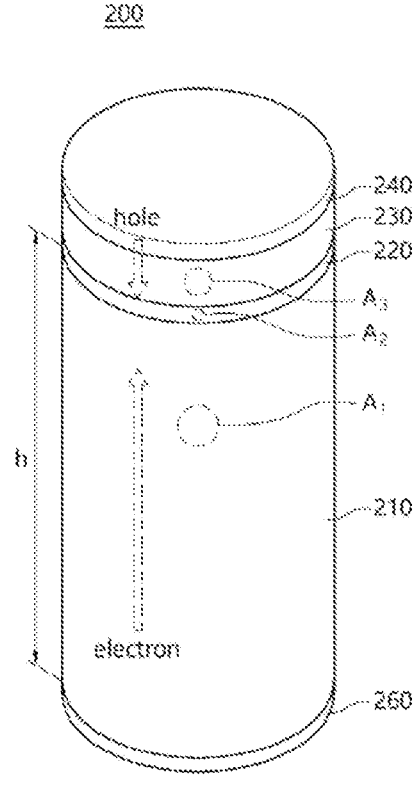
FIG. 6 is a schematic view for explaining the balance of electrons and holes in an LED device.

This will be described with reference to FIG. 6, as follows. In an LED device 200 having a diameter of about 600 nm in which an n-type GaN conductive semiconductor layer 210, a photoactive layer 220, and a p-type GaN conductive semiconductor layer 230 are stacked, when a thickness is designed in consideration of the electron mobility of the n-type GaN conductive semiconductor layer 210 and the hole mobility of the p-type GaN conductive semiconductor layer 230 so that the number of recombination electrons and the number of recombination holes at a point A2 in the photoactive layer 220 are balanced, the thickness (h) of the n-type GaN conductive semiconductor layer 210 is inevitably thicker. Therefore, unless the thickness of the p-type GaN conductive semiconductor layer 230 is implemented to be very thin, the possibility of implementing a rod-type LED device is very high. In other words, in the case of the LED device in which the thickness of each layer is designed so that the position where the number of recombination electrons and the number of recombination holes are balanced is in the photoactive layer 220, as the length of the long axis of the cross section perpendicular to the thickness direction decreases, the aspect ratio between the thickness of the LED device and the length of the long axis of the cross section becomes larger. For this reason, even if the number of recombination holes and the number of recombination electrons in the photoactive layer are balanced, it may be inappropriate to be implemented as an ink. In addition, when the thickness of the n-type GaN conductive semiconductor layer 210 is thinner to be suitable for implementation as the ink, a position where the number of recombination electrons and the number of recombination holes are balanced is a point A3 in the p-type GaN conductive semiconductor layer 230, so that the luminous efficiency may be lowered.

Figure 7:
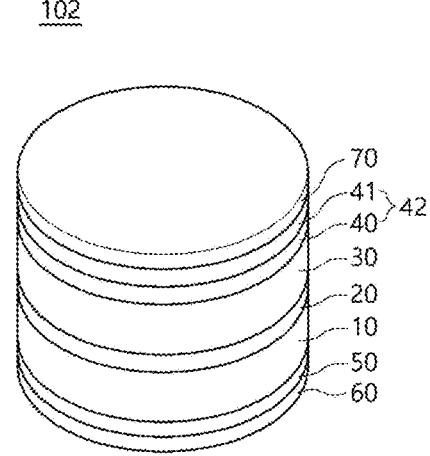
FIG. 7 is a perspective view of an ultra-thin LED device (type 1) used in an embodiment of the present invention.

Accordingly, the ultra-thin LED device provided in one embodiment of the present invention may have an electron delay layer adjacent to the n type conductive semiconductor layer in order to prevent a decrease in luminous efficiency by balancing the number of recombination holes and the number of recombination electrons in the photoactive layer while having a geometric structure suitable for implementation as an ink. Referring to FIG. 7, when the first conductive semiconductor layer is an n-type conductive semiconductor, the ultra-thin LED device 102 may include an electron delay layer 50 on the first conductive semiconductor layer 10. Through this, even if the thickness of the first conductive semiconductor layer 10 is implemented to be thin, it is possible to prevent a decrease in luminous efficiency. In addition, the reduced thickness of the first conductive semiconductor layer 10 reduces the probability that electrons are captured by surface defects while moving in the thickness direction of the first conductive semiconductor layer 10, thereby minimizing emission loss.

The electron delay layer 50 may include, for example, at least one selected from CdS, GaS, ZnS, CdSe, CaSe, ZnSe, CdTe, GaTe, SiC, ZnO, ZnMgO, $SnO_2$, $TiO_2$, $In_2O_3$, $Ga_2O_3$, Si, poly(para-phenylene vinylene) and derivatives thereof, polyaniline, poly(3-alkylthiophene), and poly(paraphenylene). In addition, the thickness of the electron delay layer 50 may be 1 to 100 nm, but is not limited thereto, and may be appropriately changed in consideration of the material of the n-type conductive semiconductor layer, the material of the electron delay layer, and the like. Hereinafter, each layer of the ultra-thin LED devices 101, 102 according to an embodiment of the present invention will be described in detail.

One of the first conductive semiconductor layer 10 and the second conductive semiconductor layer 30 may be an n-type semiconductor layer, and the other may be a p-type semiconductor layer. As the n-type semiconductor layer and the p-type semiconductor layer, a known semiconductor layer employed in a light emitting diode may be used without limitation. For example, the n-type semiconductor layer and the p-type semiconductor layer may include III-V semiconductors referred to as III-nitride materials, in particular binary, ternary and quaternary alloys of gallium, aluminum, indium and nitrogen.

For example, the first conductive semiconductor layer 10 may be an n-type semiconductor layer. In this case, the n-type semiconductor layer may have at least one of semiconductor material of InAlGaN, GaN, AlGaN, InGaN, AlN, InN, and the like, which has a composition formula of $In_xAl_yGa_{1-x-y}N$ ($0 \le x \le 1$, $0 \le y \le 1$, $0 \le x+y \le 1$), and may be doped with a first conductive dopant (e.g., Si, Ge, Sn, etc.). According to a preferred embodiment of the present invention, the thickness of the first conductive semiconductor layer 10 may be 50 to 150 nm, but is not limited thereto. In addition, the second conductive semiconductor layer 30 may be a p-type semiconductor layer. In this case, the p-type semiconductor layer may have, for example, at least one of semiconductor material of InAlGaN, GaN, AlGaN, InGaN, AlN, InN, and the like, which has the composition formula of $In_xAl_yGa_{1-x-y}N$ ($0 \le x \le 1$, $0 \le y \le 1$, $0 \le x+y \le 1$), and may be doped with a second conductive dopant (e.g., Mg). According to a preferred embodiment of the present invention, the thickness of the second conductive semiconductor layer 30 may be 100 to 1800 nm, but is not limited thereto.

Also, the photoactive layer 20 positioned between the first conductive semiconductor layer 10 and the second conductive semiconductor layer 30 may have a single or multiple quantum well structure. As the photoactive layer 20, a photoactive layer included in a typical LED device used for lighting, display, and the like may be used without limitation. A clad layer (not shown) doped with a conductive dopant may be formed above and/or below the photoactive layer 20, and the clad layer doped with the conductive dopant may be implemented as an AlGaN layer or an InAlGaN layer. In addition, a material such as AlGaN or AlInGaN may be used as the photoactive layer 20. When an electric field is applied to the device, the electrons and holes that move from the conductive semiconductor layers each positioned above and below the photoactive layer to the photoactive layer generate electron-hole pairs in the photoactive layer 20, so emission is occurred. According to a preferred embodiment of the present invention, the thickness of the photoactive layer 20 may be 50 to 200 nm, but is not limited thereto.

Meanwhile, the upper electrode layer 60 may be provided under the above-described first conductive semiconductor layer 10. Alternatively, the electron delay layer 50 may be further provided between the first conductive semiconductor layer 10 and the upper electrode layer 60. In addition, the lower electrode layer 40 may be provided on the above-described second conductive semiconductor layer 30.

As the lower electrode layer 40 and the upper electrode layer 60, an electrode layer included in a typical LED device may be used without limitation. The lower electrode layer 40 and the upper electrode layer 60 may be each independently a single layer formed of one or a mixture of two or more of Cr, Ti, Al, Au, Ni, ITO, oxides thereof and alloys thereof, or a composite layer composed in which each of two or more of the above materials is layered. For example, the ultra-thin LED device 102 may include a lower electrode layer 42 in which an ITO electrode layer 40 and a Ti/Au composite layer 41 are stacked on the second conductive semiconductor layer 30 as shown in FIG. 4. In addition, the lower electrode layer 40 and the upper electrode layer 60 may each independently have a thickness of 10 to 500 nm, but is not limited thereto.

In addition, on one side in the thickness direction of the ultra-thin LED device and either one or both sides of the disposing areas $(S_1, S_2, S_3, S_4)$ where the ultra-thin LED devices are to be disposed in the lower electrodes 311, 312, an arrangement inducing layer for arranging the ultra-thin LED device upright in the thickness direction may be formed. The arrangement inducing layer induces the ultra-thin LED device 101 to move onto a desired region on the lower electrodes 311, 312, for example, the disposing areas $(S_1, S_2, S_3, S_4)$, and serves to erect the ultra-thin LED device 101 on the lower electrodes 311, 312 to be disposed. The arrangement inducing layer may be formed on the side of the ultra-thin LED device 101 and/or on a desired region on the lower electrodes 311, 312, for example, on the disposing areas $(S_1, S_2, S_3, S_4)$.

A case where the arrangement inducing layer is formed only on the lower electrodes 311, 312 will be described as follows. The arrangement inducing layer in this case may be a binding layer that is chemically bounded to the metal part of the ultra-thin LED device 101, for example, the lower electrode layer and/or the upper electrode layer. In this case, the binding layer may be, for example, a layer formed so that a thiol group is exposed to the outside.

Figure 5A:
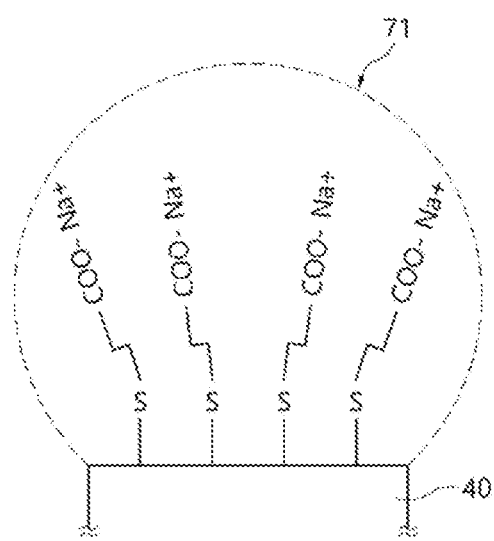
FIGS. 5A to 5C are views of various embodiments of an arrangement inducing layer that may be provided in an ultra-thin LED device (type 1) used in an embodiment of the present invention.
Figure 5B:
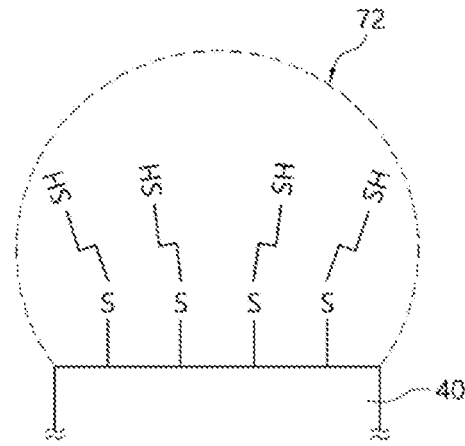
Figure 5C:
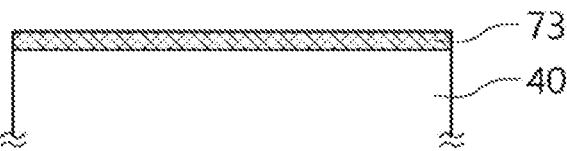

In addition, a case where the arrangement inducing layer is formed on the ultra-thin LED device 101 will be described as follows. An arrangement inducing layer 70 may be further included on the lower electrode layer 40 as shown in FIGS. 3 and 5*a* to 5*c*. The material of the arrangement inducing layer 70 may vary according to a specific induction and coupling method. For example, the arrangement inducing layer 70 may be a charge layer having a positive or negative charge, and specifically, the charge layer 71 having a negative charge as shown in FIG. 5*a*. The charge layer 71 may be assembled by inducing and erecting the ultra-thin LED device onto the lower electrode through an electrophoresis method, which will be described later. Alternatively, as shown in FIG. 5*b*, the arrangement inducing layer may be a binding layer 72, and the functional group exposed to the binding layer 72 may form a chemical bond with other functional groups provided on the first electrode, or may be bound through a chemical bond, for example, adsorption on the lower electrode of metal material. In addition, the arrangement inducing layer 70 may be a magnetic layer 73 as shown in FIG. 5*c*, and the magnetic layer 73 may be assembled on the lower electrodes 311, 312 under a magnetic field.

On the other hand, when the arrangement inducing layer 70 provided on the ultra-thin LED device is the charge layer 71, a charge layer having a charge opposite to that of the charge layer 71 provided in the ultra-thin LED device may be further provided in the disposing area in the lower electrodes 311, 312. Through this, there is the advantage of better inducing the ultra-thin LED device to the disposing area and better inducing the ultra-thin LED device upright. The charge layer is not limited if it is formed of a material suitable for forming a layer or a film while having a positive or negative charge.

In addition, even when the arrangement inducing layer 70 provided on the ultra-thin LED device is the magnetic layer 73, a magnetic layer may be further included on the disposing area within the lower electrode 311, 312. Through this, it has the advantage of better inducing the ultra-thin LED device to the disposing area while better inducing the ultra-thin LED device upright. The magnetic layer may be a ferromagnetic material or a paramagnetic material.

Figure 4:
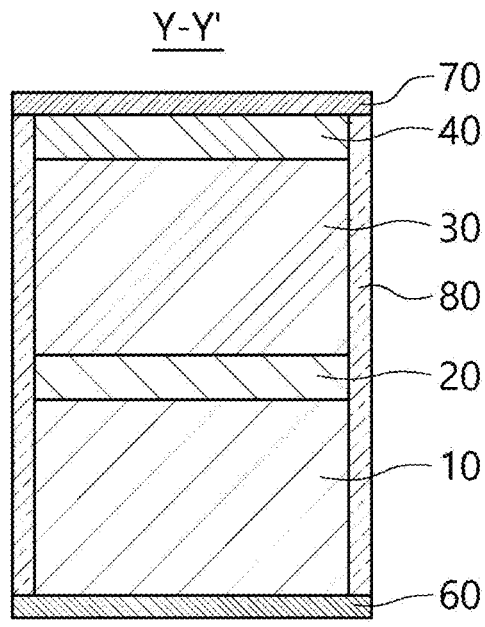
FIG. 4 is a cross-sectional view taken along the line Y-Y' of FIG. 3.

Meanwhile, in FIGS. 3 and 4, the arrangement inducing layer 70 is shown to be positioned on the lower electrode layer 40, but is not limited thereto, and may be disposed to be positioned on the upper electrode layer 60. In other words, the arrangement inducing layer 70 may be provided in the ultra-thin LED device so as to be on either side in the thickness direction of the ultra-thin LED device, that is, the uppermost layer or the lowermost layer.

In addition, the ultra-thin LED device 101 may further include a protective film 80 surrounding the side surface of the device when a plane parallel to the stacking direction is referred to as a side surface. The protective film 80 serves to protect the surfaces of the first conductive semiconductor layer 10, photoactive layer 20, and second conductive semiconductor layer 30. In addition, after etching the LED wafer in the thickness direction as in a method of manufacturing an ultra-thin LED device to be described later, it can serve to protect the first conductive semiconductor layer 10 in the process of separating a plurality of LED pillars.

The protective film 80 may include, for example, at least one selected from $Si_3N_4$, $SiO_2$, $Al_2O_3$, $HfO_2$, $ZrO_2$, $Y_2O_3$, $TiO_2$, AlN, and GaN. The thickness of the protective film 5 may be 5 nm to 100 nm, more preferably 30 nm to 100 nm, which may be advantageous in protecting the first conductive semiconductor layer 10 in the process of separating LED pillar to be described later.

Figure 8:
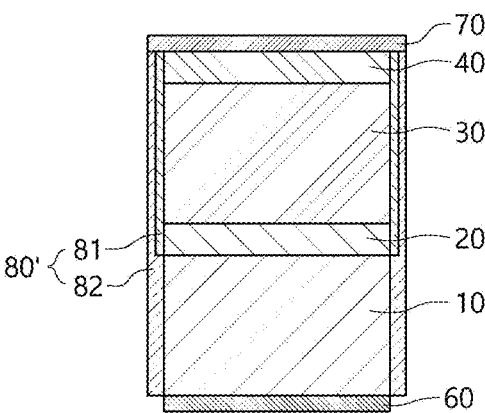
FIG. 8 is a cross-sectional view of an ultra-thin LED device (type 1) used in an embodiment of the present invention.

On the other hand, as shown in FIG. 8, in order to have improved luminous efficiency in addition to a protective function as a protective film, the ultra-thin LED device 103 according to an embodiment of the present invention may include a protective film 80' composed of a hole pushing film 81 that surrounds an exposed side surface of the second conductive semiconductor layer 30 or the exposed side surface of the second conductive semiconductor layer 30 and the exposed side surface of at least a portion of the photoactive layer 20 to move the holes on the exposed side surface toward the center; and an electron pushing film 82 that surrounds the exposed side surface of the first conductive semiconductor layer 10 to move the electrons on the exposed side surface toward the center.

Some of the charges moving from the first conductive semiconductor layer 10 to the photoactive layer 20 and some of the holes moving from the second conductive semiconductor layer 30 to the photoactive layer 20 may move along the side surface. However, in this case, quenching of electrons or holes occurs due to defects present on the surface, which may reduce luminous efficiency. In this case, even when the protective film is provided, there is an unavoidable problem of quenching due to defects occurring on the surface of the device before the protective film is provided. However, when the protective film 80' is composed of the hole pushing film 81 and the electron pushing film 82, the electrons and holes are concentrated toward the center of the device to induce them to move in the direction of the photoactive layer, so even if defects occur on the surface of the device before the protective film is formed, there is an advantage in that loss of luminous efficiency due to surface defects can be prevented.

The hole pushing film 81 may include, for example, at least one selected from the group consisting of $AlN_x$, $ZrO_2$, MoO, $Sc_2O_3$, $La_2O_3$, MgO, $Y_2O_3$, $Al_2O_3$, $Ga_2O_3$, $TiO_2$, ZnS, $Ta_2O_5$ and n-$MoS_2$. The electron pushing film 82 may include at least one selected from the group consisting of $Al_2O_3$, $HfO_2$, $SiN_x$, $SiO_2$, $ZrO_2$, $Sc_2O_3$, $AlN_x$ and $Ga_2O_3$.

In addition, as shown in FIG. 8, when the ultra-thin LED device includes both the hole pushing film 81 and the electron pushing film 82, the electron pushing film 82 may be provided as an outmost film surrounding the surfaces of the first conductive semiconductor layer 10, photoactive layer and second conductive semiconductor layer 30.

In addition, the hole pushing film 81 and the electron pushing film 82 may each independently have a thickness of 1 to 50 nm.

On the other hand, the first conductive semiconductor layer 10, photoactive layer 20, and second conductive semiconductor layer 30 of the above-described ultra-thin LED device may be included as a minimum component of the ultra-thin LED device, and it should be noted that another phosphor layer, quantum dot layer, active layer, semiconductor layer, hole blocking layer and/or electrode layer may be further included on/below each of the layers.

The above-described ultra-thin LED electrode assembly 1000 may be manufactured by a manufacturing method to be described later. Specifically, the ultra-thin LED electrode assembly 1000 may be manufactured by the method including the steps of (1) preparing a lower electrode line including a lower electrode; (2) processing on the lower electrode an ink composition including a plurality of ultra-thin LED devices including the stacked first conductive semiconductor layer, photoactive layer, and second conductive semiconductor layer and having a ratio between the thickness in the stacking direction and the length of the long axis in the cross section perpendicular to the stacking direction is 1:0.5 to 1.5 or 1:1.5 to 5.0; (3) erecting and assembling the ultra-thin LED devices on the lower electrode in the thickness direction; (4) filling the periphery of the ultra-thin LED devices with an insulator; and (5) forming an upper electrode line including an upper electrode so as to be electrically connected to the opposite side of the ultra-thin LED devices opposite to the one side. Hereinafter, a description of the ultra-thin LED electrode assembly 1000 described above in the description of the manufacturing method will be omitted.

As step 1 according to the present invention, the step of preparing the lower electrode line 310 including the lower electrodes 311, 312 is performed.

The lower electrodes 311, 312 may be implemented with various known electrode patterns through a known method, and the present invention is not particularly limited thereto. For example, as shown in FIG. 1, a plurality of lower electrodes 311, 312 may be implemented in a pattern in which they are spaced apart at a predetermined interval and arranged in parallel. The lower electrodes 311, 312 may be formed on a substrate 400, and the substrate 400 may be, for example, any one of a glass substrate, a quartz substrate, a sapphire substrate, a plastic substrate, and a bendable flexible polymer film. As another example, the substrate 400 may be transparent. However, it is not limited to the listed types, and any substrate capable of forming an electrode may be used.

The area of the substrate 400 is not limited and may be changed in consideration of the area of the lower electrodes 311, 312 formed on the substrate 400. In addition, the thickness of the substrate 400 may be 100 μm to 1 mm, but is not limited thereto.

Next, as step 2 according to the present invention, the step of processing the ink composition on the lower electrodes 311, 312 is performed. The ink composition includes the plurality of the ultra-thin LED devices 101 having the stacked first conductive semiconductor layer 10, photoactive layer 20, and second conductive semiconductor layer 30 and the ratio between the thickness in the stacking direction and the length of the long axis in the cross section perpendicular to the stacking direction of 1:0.5 to 1.5 or 1:1.5 to 5.0.

The plurality of ultra-thin LED devices 101 is prepared as the ink composition that is ink-formed. The ultra-thin LED device assembly 100 made of the plurality of ultra-thin LED devices 101 is manufactured by the manufacturing method 1 shown in FIGS. 9 and 10 or the manufacturing method 2 shown in FIG. 11. The manufacturing method 1 may be usefully selected when the n-type III-nitride semiconductor layer is a doped n-type III-nitride semiconductor layer, and the manufacturing method 2 may be usefully selected when the n-type III-nitride semiconductor layer is not doped.

The manufacturing method 1 and the manufacturing method 2 are common up to the process for preparing the wafer (100*h* in FIG. 9, 100*h* in FIG. 11) including the plurality of LED structures from an LED wafer 100*a*, and are different in the process of separating the formed LED structure from the wafer. The process of preparing the wafer (100*h* in FIG. 9, 100*h* in FIG. 11) including the plurality of LED structures from the LED wafer 100*a* will be described through the manufacturing method 1.

First, the manufacturing method 1 will be described with reference to FIG. 9. The manufacturing method 1 may include the steps of (A) preparing the LED wafer 100*a* ((a) in FIG. 9), (B) forming the plurality of LED structures by patterning the upper portion of the LED wafer 100*a* so that a plane perpendicular to the direction in which the layers are stacked in each LED structure has a desired shape and size ((b), (c) in FIG. 9) and etching in the vertical direction to at least a partial thickness of the first conductive semiconductor layer 10 ((d) to (h) in FIG. 9), (C) forming a protective film that surrounds the exposed surface of each of the plurality of LED structures while the upper surface of a first portion between the adjacent LED structures being exposed to the outside ((i) to (j) in FIG. 9), (D) forming a plurality of pores in the first portion by applying power after immersing the LED wafer in an electrolyte, electrically connecting the LED wafer to any one terminal of a power source, and electrically connecting the other terminal of the power source to the electrode immersed in the electrolyte ((k) in FIG. 9) and (E) separating the plurality of LED structures from the first portion in which the plurality of pores is formed by applying ultrasonic waves to the LED wafer ((o) in FIG. 9).

As the LED wafer 100*a* prepared in step A, commercially available ones may be used without limitation. For example, the LED wafer 100*a* may include the substrate 1, the first conductive semiconductor layer 10, the photoactive layer 20, and the second conductive semiconductor layer 30 at a minimum. In this case, the first conductive semiconductor layer 10 may be an n-type III-nitride semiconductor layer, and the second conductive semiconductor layer 30 may be a p-type III-nitride semiconductor layer. In addition, since the LED structure remaining on the LED wafer after etching the n-type III-nitride semiconductor layer to a desired thickness can be separated through steps (C) to (E), the thickness of the n-type III-nitride semiconductor layer in the LED wafer is also not limited, and the presence or absence of a separate sacrificial layer may not be considered when selecting a wafer.

In addition, each layer in the LED wafer 100*a* may have a c-plane crystal structure.

In addition, the LED wafer 100*a* may have undergone a cleaning process, and since a commonly employed wafer cleaning solution and cleaning process may be appropriately employed as for the cleaning process, the present invention is not particularly limited thereto. The cleaning solution may be, for example, isopropyl alcohol, acetone and hydrochloric acid, but is not limited thereto.

Next, before step B is performed, the step of forming the lower electrode layer 40 on the second conductive semiconductor layer 30 which is a p-type III-nitride semiconductor layer may be performed. The lower electrode layer 40 may be formed by a commonly employed method of forming an electrode on a semiconductor layer, and may be formed by, for example, deposition through sputtering. The material of the lower electrode layer 40 may be, for example, ITO as described above, and may be formed to have a thickness of about 150 nm. The lower electrode layer 40 may be further subjected to a rapid thermal annealing process after the deposition process. For example, the lower electrode layer 40 may be treated at 600° C. for 10 minutes, but may be appropriately adjusted in consideration of the thickness and material of the electrode layer, so the present invention is not particularly limited thereto.

Figures 9A, 9R:
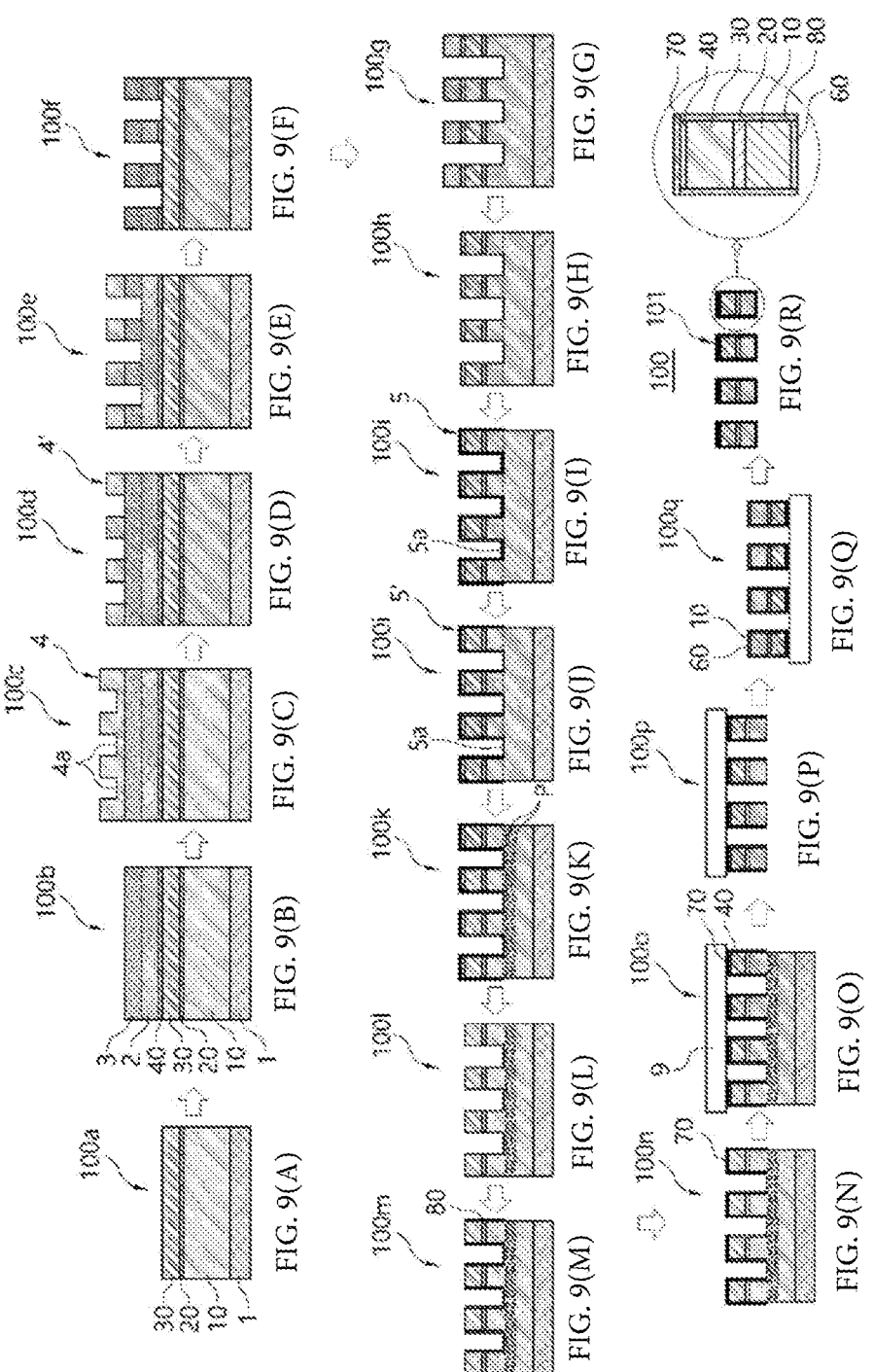
FIGS. 9(A) to 9(R) and 10(A) to 10(F) are schematic views of a device structure at different respective points in a method 1 for manufacturing an ultra-thin LED device (type 1) used in an embodiment of the present invention.

Next, as step B, the upper portion of the LED wafer can be patterned so that a plane perpendicular to the direction in which the layers are stacked in a single LED structure has a desired shape and size ((b) to (c) in FIG. 9). Specifically, a mask pattern layer may be formed on the upper surface of the lower electrode layer 40, and the mask pattern layer may be formed of a known method and material used in etching an LED wafer, and the pattern of the pattern layer may be formed by appropriately applying a commonly employed photolithography or nanoimprinting method, and the like.

For example, the mask pattern layer may be a stacked body of a first mask layer 2, second mask layer 3, and resin pattern layer 4' forming a predetermined pattern on the lower electrode layer 40 as shown in (f) in FIG. 9. The method of forming the mask pattern layer is briefly described. For example, the first mask layer 2 and the second mask layer 3 are formed on the lower electrode layer 40 through vapor deposition. After forming the resin layer 4, which is the origin of the resin pattern layer 4', on the second mask layer 3 ((b), (c) in FIG. 9), a resin remaining portion 4a of the resin layer 4 is removed by a commonly employed method such as a reactive ion etching (ME) ((d) in FIG. 9). Then, the mask pattern layer may be formed by sequentially etching each of the second mask layer 3 and the first mask layer 2 along the pattern of the resin pattern layer 4' ((e), (f) in FIG. 9). In this case, the first mask layer 2 may be formed of, for example, silicon dioxide, and the second mask layer 3 may be a metal layer such as aluminum or nickel, and their etching is performed by RIE and inductively coupled plasma (ICP), respectively. Meanwhile, when the first mask layer 2 is etched, the resin pattern layer 4' may also be removed (see 100f).

In addition, the resin layer 4 from which the resin pattern layer 4' is derived may be formed through a nanoimprinting method. After preparing a mold corresponding to a desired predetermined pattern template, the resin layer is formed by treating the mold with a resin. The resin layer 4 is transferred so that the resin layer is positioned on the wafer stack 100b in which the first mask layer 2 and the second mask layer 3 are formed on the lower electrode layer 40, the mold is removed, so that the wafer stack 100c in which the resin layer 4 is formed can be implemented.

On the other hand, although a method of forming a pattern through a nanoimprinting method has been described, the present invention is not limited thereto. The pattern may be formed through photolithography using a known photosensitive material, or may be formed through known laser interference lithography, electron beam lithography, or the like.

Thereafter, as shown in (g) in FIG. 9, by etching to a partial thickness of the first conductive semiconductor layer 10, which is an n-type III-nitride semiconductor layer, in a direction perpendicular to the surface of the LED wafer 100f, according to the pattern of the mask pattern layers 2, 3 formed on the lower electrode layer 40, an LED wafer 100g on which an LED structure is formed may be manufactured. In this case, the etching can be performed through a typical drying etching method such as ICP and KOH/TAMH wet etching. In this etching process, the second mask layer 3 that is Al constituting the mask pattern layer may be removed, and then the first mask layer 2 that is silicon dioxide constituting the mask pattern layer present on the lower electrode layer 40 of each LED structure in the LED wafer 100g may be removed. Through this, the LED wafer 100h in which the plurality of LED structures is formed can be prepared.

As step C, the step of forming a protective film 80a that surrounds the exposed surface of each of the plurality of LED structures by a predetermined thickness in the LED wafer 100h on which the plurality of LED structures is formed, while exposing the upper surface ($S_1$) of a first portion (a) between the adjacent LED structures to the outside is formed ((i), (j) in FIG. 9). The protective film 80a is to prevent damage to the LED structure due to the execution of step D, which will be described later. In addition, when the protective film is continuously remained on the side of the LED structure separated from the LED wafer, it can even protect the side surface of the individually separated LED structure from external stimuli.

Steps C to E will be described with reference to FIG. 10. Specifically, step C may be performed by depositing a protective film material on the LED wafer 100h on which the plurality of LED structures is formed so that the protective film 80a surrounds the exposed surface of each of the plurality of LED structures by a predetermined thickness (step C-1) and removing the protective film deposited on the upper surface ($S_1$) of the first portion (a) between the adjacent LED structures to expose the upper surface ($S_1$) of the first portion (a) between the LED structures to the outside (step C-2).

Figures 10A, 10B, 10C, 10D, 10E, 10F:
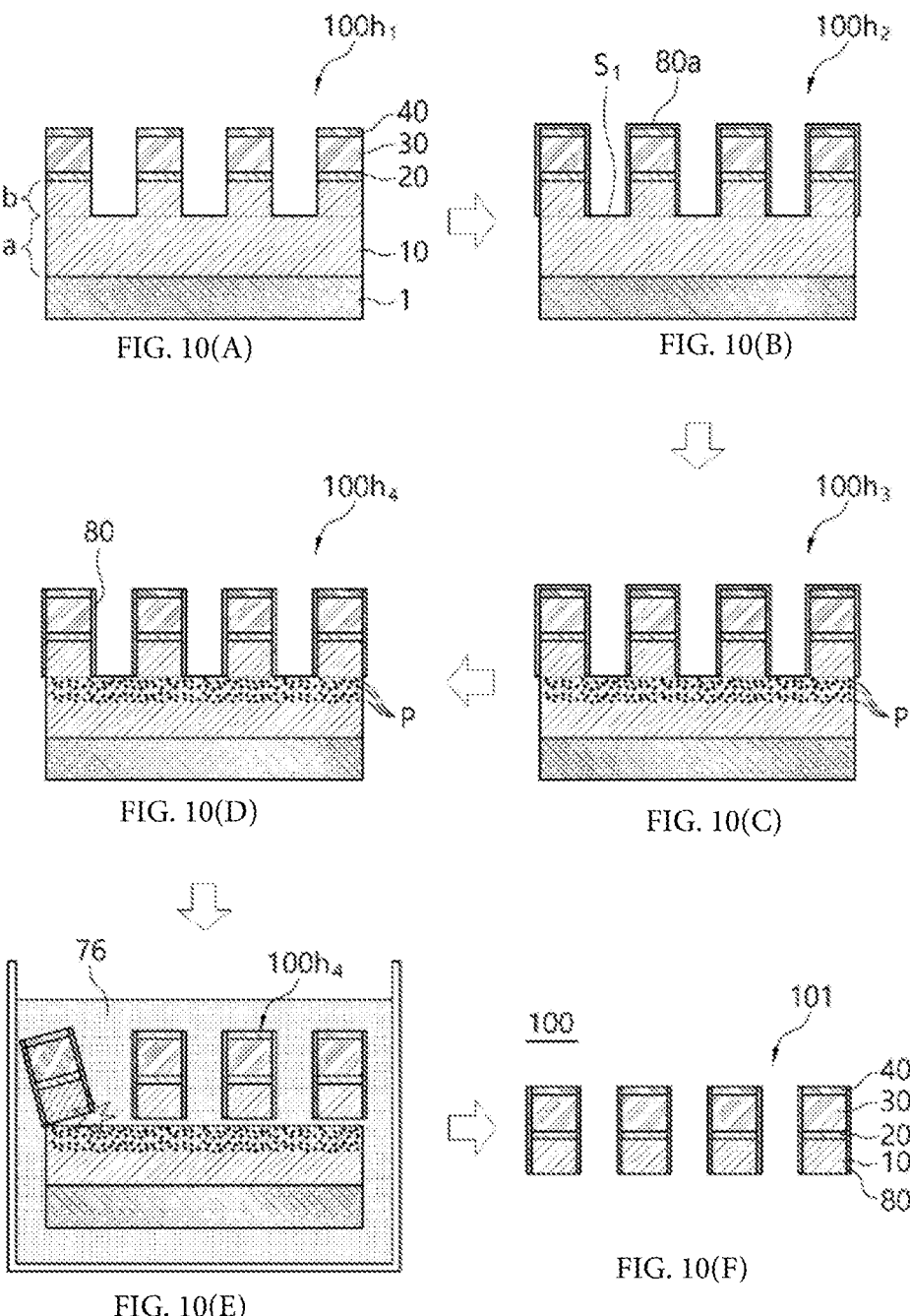

Step C-1 is a step of depositing the protective film material on the LED wafer 100h on which the plurality of LED structures is formed ((a) in FIG. 10). In this case, the protective film material may be a known material that is not chemically affected by the electrolyte of step 4 to be described later. For example, as the protective film material, the material of the aforementioned protective film 80 can be used without limitation. For example, the protective film material may include at least one from silicon nitride ($Si_3N_4$), silicon dioxide ($SiO_2$), aluminum oxide ($Al_2O_3$), hafnium oxide ($HfO_2$), zirconium oxide ($ZrO_2$), yttrium oxide ($Y_2O_3$), lanthanum oxide ($La_2O_3$), scandium oxide ($Sc_2O_3$), titanium dioxide ($TiO_2$), aluminum nitride (AlN) and gallium nitride (GaN). In addition, the thickness of the protective film 80a formed through deposition of the protective film material may be 5 to 100 nm, more preferably 30 to 100 nm. If the thickness of the protective film 80a is less than 5 nm, it may be difficult to prevent the invasion of the electrolyte on the LED structure in step D to be described later, and if the thickness exceeds 100 nm, there may be problem with increased manufacturing cost, or connection between the LED structures.

Next, step C-2 is the step of removing the protective film deposited on the upper surface ($S_1$) of the first portion (a) between the adjacent LED structures to expose the upper surface ($S_1$) of the first portion (a) between the LED structures to the outside ((b) in FIG. 10). Due to the execution of step C-1, the protective film material is also deposited on the upper surface ($S_1$) of the first portion (a) between the adjacent LED structures. Due to this, the electrolyte may not contact the first conductive semiconductor layer 10 which is an n-type III-nitride semiconductor, and thus, it may not be possible to form desired pores in the first portion (a). Accordingly, the step of removing the protective film material coated on the upper surface ($S_1$) of the first part (a) to expose the upper surface to the outside is performed. In this case, the removal of the protective film material may be performed through a known dry or wet etching method in consideration of the protective film material.

On the other hand, according to an embodiment of the present invention, the protective film 80a formed in step C is a temporary protective film for preventing damage to the LED structure due to performing step C. Between steps D and E, the step of forming a surface protective film surrounding the side surface of the LED structure may be further included after removing the temporary protective film. That is, as shown in FIG. 9, the protective film 5' in step 3 is provided only as a temporary protective film for preventing damage to the LED structure in step 4 ((i) to (k) in FIG. 9), and is removed before performing step 5, so that the surface protective film 80 for performing a function of preventing damage to the surface of the LED structure may be formed to cover the side surface of the LED structure ((m) in FIG. 9).

On the other hand, some embodiments as shown in FIG. 9 have the inconvenience of forming the protective film twice, but may be selected in consideration of the planar shape, size, and spacing between the LED structures to be manufactured. In addition, when performing step D, which will be described later, the protective film may be partially invaded. If using the invaded protective film as a surface protective film by leaving the invaded protective film on the finally obtained individual LED structure, there may be cases in which it may be difficult to properly perform the surface protection function. Therefore, in some cases, it may be advantageous to provide a protective film again after removing the protective film that has undergone step D.

The manufacturing process shown in FIG. 9 as such will be described. The temporary protective film material 5 is deposited on the LED wafer 100h on which the plurality of LED structures is formed ((i) in FIG. 9), and then the protective film 5', which is the temporary protective film that protects the side surfaces and upper portion of the plurality of LED structures may be formed by etching the temporary protective material 5 on the upper surface ($S_1$) of the first portion (a) of the first conductive semiconductor layer 10, which is a doped n-type III-nitride semiconductor layer between adjacent LED structures of the LED wafer 100i on which the protective coating material 5 is deposited. After performing the step D to be described later ((k) in FIG. 9), the protective film 5' is removed through etching ((l) in FIG. 9). Then, as a surface protective film for protecting the surface of the LED structure, the protective film material is deposited on the LED wafer 100l, and then the protective film material formed on each of the LED structures is removed to form the protective film 80 surrounding the side surface of the LED structure ((m) in FIG. 9). In this time, not only the protective film material formed on the LED structure, but also the protective film material deposited on the upper portion ($S_1$) of the first portion (a) of the first conductive semiconductor layer 10, which is a doped n-type III-nitride semiconductor layer, between adjacent LED structures of the LED wafer 100m may be removed. Through this, in step 3 to be described later, a foaming solvent can contact the upper surface ($S_1$) of the first part (a), and the foams generated through ultrasonic waves penetrate into the pores (P) formed in the first portion (a), so that the LED structures can be separated through the foams.

On the other hand, the temporary protective film material and the surface protective film material are the same as the material of the above-described protective film, and the thickness of the film to be implemented may also be implemented within the thickness range of the above-described protective film.

Next, as step D of the manufacturing method 1, the step of forming a plurality of pores in the first portion by applying power after immersing the LED wafer in an electrolyte, electrically connecting the LED wafer to any one terminal of a power source, and electrically connecting the other terminal of the power source to the electrode immersed in the electrolyte.

Specifically, with reference to FIG. 10, the LED wafer 100$h_2$ on which the protective film 80a is formed is electrically connected to one terminal of a power source, for example, an anode, and the electrode immersed in the electrolyte is electrically connected to the other terminal of the power source, for example, a cathode. Then, by applying power, an LED wafer 100$h_3$ having a plurality of pores (Ps) formed in the first portion (a) of the first conductive semiconductor layer 10, which is an n-type III-nitride semiconductor doped, may be prepared. In this case, the pores (Ps) may be formed from the upper surface ($S_1$) of the first portion (a) of the first conductive semiconductor layer 10, which is a doped n-type III-nitride semiconductor that is in direct contact with the electrolyte, in the thickness direction and in a lateral direction of the first portion (a) corresponding to the lower portion of each of the plurality of LED structures.

The electrolyte used in step D may include at least one oxygen acid selected from the group consisting of oxalic acid, phosphoric acid, sulfurous acid, sulfuric acid, carbonic acid, acetic acid, chlorous acid, chloric acid, bromic acid, nitrous acid and nitric acid. More preferably, for example, oxalic acid can be used as the electrolyte. Therefore, there is an advantage in that damage to the first conductive semiconductor layer can be minimized. In addition, the electrode may be made of platinum (Pt), carbon (C), nickel (Ni), gold (Au), or the like, and may be, for example, a platinum electrode. In addition, in step D, a voltage of 3 V or more can be applied as a power source for 1 minute to 24 hours, through which the pores (Ps) are smoothly formed up to the first portion (a) corresponding to the lower portion of each of the plurality of LED structures. Accordingly, the LED structure can be easily separated from the wafer through step E. More preferably, the voltage may be 10V or more, and more preferably, the voltage of 30V or less may be applied.

If the voltage is less than 3V, even if the application time of the power is increased, the formation of pores on the first portion (a) corresponding to the lower portion of each LED structure is not smooth, so it is difficult to separate the LED structure through step E described later. Even if separated, the shape of the separated cross section of each of the plurality of LED structures may be different, and thus, it may be difficult for the plurality of LED structures to exhibit uniform characteristics. In addition, when the voltage in excess of 30V is applied, pores may be formed up to the second portion (b), which is the lower end of the LED structure following the first portion (a) of the doped n-type III-nitride semiconductor layer, thereby causing the deterioration of luminescent properties. In addition, it is preferable that the separation of the LED structure in step E to be described later is made at the boundary point between the first portion (a) and second portion (b) of the doped n-type III-nitride semiconductor layer. However, due to the pores formed on the second portion (b), separation may occur at any point on the second portion (b) outside the boundary point, so there is a risk that the LED structure having an n-type semiconductor layer with a thickness thinner than the thickness of the initially designed n-type semiconductor layer is obtained. In addition, similarly to the effect according to the strength of the voltage, if the application time of the power is increased, there is a risk that pores are formed up to the second portion (b) other than the desired portion. Conversely, if the application time is short, separation of the LED structure may be difficult due to poor pore formation.

After step D and before step E to be described later, it may perform the step of preparing an LED wafer $100h_4$ on which the protective film formed on the upper surface of each of the LED structures, among the protective film $80a$, is removed so that the LED structure can be electrically connected to the lower electrode layer $40$ after the LED structure is separated from the wafer. In addition, since only the protective film formed on the upper surface of the LED structure is removed, the protective film $80$ formed on the side surface of the LED structure remains, thereby protecting the side surface of the LED structure from the outside.

In addition, after step D and before step E to be described later, the step of forming another layer on the lower electrode layer $40$ of the LED structure may be further performed. The other layer may be, for example, a Ti/Au composite layer that may be further formed as a lower electrode layer material on the lower electrode layer $40$, which is an ITO layer, or the arrangement inducing layer $70$ (see (n) in FIG. 9).

Next, as step E according to the manufacturing method 1, the step of separating the plurality of LED structures from the first portion (a) in which the plurality of pores (Ps) is formed by applying ultrasonic waves to the LED wafer $100h_4$ may be performed. In this case, the ultrasonic wave may be directly applied to the pore-formed LED wafer $100h_4$ or may be indirectly applied by immersing the pore-formed LED wafer $100h_4$ in a solvent. However, in the method of collapsing the pores (Ps) of the first portion (a) using the physical external force caused by the ultrasonic wave itself, the collapse of the pores is not smooth, and if the pores are excessively formed to facilitate the collapse, there is a possibility that pores may be formed up to the second portion (b) of the LED structure, which may cause a side effect of reducing the quality of the LED structure.

Accordingly, according to an embodiment of the present invention, step E may be performed using a sonochemistry method, and specifically, the LED wafer $100h_4$ is immersed in a foam forming solution (or solvent) $76$. Then, the plurality of LED structures can be separated by applying ultrasonic waves to the foam forming solution (or solvent) $76$ to collapse the pores through the energy generated when the foams generated and grown by the sonochemical mechanism burst from the pores. This will be described in detail. Ultrasonic waves alternately generate a relatively high pressure part and a relatively low pressure part in the direction of sound wave travel. The generated foams pass through the high pressure part and the low pressure part, repeat compression and expansion, grow into foams having a higher temperature and pressure, and then collapse. When the foams collapse, it becomes a local hot spot that generates a high temperature of 4000K level and a high pressure of 1000 atmospheric pressure level, for example. Using this energy, the pores generated in the LED wafer collapse and the LED structure can be separated from the wafer. After all, the ultrasonic wave generates and grows foams in the foam forming solution (or solvent), and only functions to move and penetrate the generated foams into the pores (Ps) of the first portion (a). After that, the plurality of LED structures can be easily separated from the LED wafer through a pore collapse mechanism in which pores (Ps) are collapsed by an external force generated when the foams in an unstable state with high temperature and pressure that have penetrated the pores (P) burst. Accordingly, an LED assembly $100'$ including the plurality of ultra-thin LED devices $101'$ can be obtained.

The foam forming solution (or solvent) $76$ generates foams when ultrasonic waves are applied, and as the foam forming solution, a solution (or solvent) that can be grown to have a high pressure and temperature can be used without limitation. Preferably, the foam forming solution (or solvent) having a vapor pressure of 100 mmHg (20° C.) or less, as another example, 80 mmHg (20° C.) or less, 60 mmHg (20° C.) or less, 50 mmHg (20° C.) or less, 40 mmHg (20° C.) or less, 30 mmHg (20° C.) or less, 20 mmHg (20° C.) or less, or 10 mmHg (20° C.) or less can be used. If a solvent having a vapor pressure exceeding 100 mmHg (20° C.) is used, separation may not occur properly within a short time, thereby prolonging the manufacturing time and increasing the production cost. The foam forming solution $76$ satisfying these physical properties may be, for example, at least one selected from the group consisting of gamma-butyllactone, propylene glycol methyl ether acetate, methyl pyrrolidone, and 2-methoxyethanol. On the other hand, a solution (or solvent) having a vapor pressure of 100 mmHg at room temperature, for example, 20° C. may be used as the foam forming solution (or solvent). It should be noted that step E may be performed by adjusting the conditions of step E, for example, the vapor pressure of the form forming solution (or solvent) to be 100 mmHg or less (e.g., low temperature conditions, etc.). In this case, The range of solvents that can be used can be broadened, and solvents such as water, acetone, chloroform, and alcohol may be used as an example.

In addition, the wavelength of the ultrasonic wave applied in step E may be applied at a frequency range that can cause sonochemistry, specifically to grow and collapse the foams so that it becomes a local hotspot that generates high pressure and temperature when the foams collapses. For example, the frequency may be 20 kHz to 2 MHz, and the application time of the applied ultrasonic wave may be 1 minute to 24 hours. Though this, the LED structure can be easily separated from the LED wafer. Even if the wavelength of the applied ultrasonic wave falls within the range, if the intensity is low or the application time is short, there is a risk that an LED structure that is not separated from the LED wafer exists or the number of LED structures that is not separated from the LED wafer is increased. In addition, if the intensity of the applied ultrasonic wave is large or the application time is long, the LED structure may be damaged.

On the other hand, in order to form the upper electrode layer $60$ on the first conductive semiconductor layer $10$, before performing the above-described step E, the step of attaching the support film $9$ on the LED wafer $100n$ may be further preformed to form another layer, for example, the upper electrode layer $60$ or the electron delay layer (not shown) on the first conductive semiconductor layer $10$. Thereafter, by performing step E, the plurality of LED structures can be separated in a state in which the support film $9$ is attached ((p) in FIG. 9). After forming the upper electrode layer $60$ on the upper surfaces of the plurality of LED structures through a known method such as deposition in a state in which the support film $9$ is attached ((q) in FIG. 9), the assembly $100$ of the plurality of ultra-thin LED devices $101$ can be obtained when removing the support film.

Next, a method for manufacturing an ultra-thin LED device through manufacturing method 2 will be described with reference to FIG. 11.

The manufacturing method of an LED wafer $100h$ on which a plurality of LED structures is formed from a LED wafer as described above is the same as in the manufacturing method 1. Thereafter, the LED wafer $100h$ on which a plurality of LED structures is formed is manufactured by a process including the steps of (i) forming an insulating film 8 to cover the exposed side surfaces of the plurality of LED structures ((b) in FIG. 11), (ii) removing a portion of the insulating film 8 formed on the first conductive semiconductor layer 10 to expose the upper surface (S₁) of the first conductive semiconductor layer 10 between the adjacent LED structures ((c) in FIG. 11), (iii) forming a portion of the first conductive semiconductor layer whose side surface is exposed by a predetermined thickness below the first conductive semiconductor layer of the LED column on which the insulating film 8' is formed, by further etching the first conductive semiconductor layer 10 in the thickness direction through the exposed upper portion (S₁) of the first conductive semiconductor layer ((c) in FIG. 11), (iv) etching the portion of the first conductive semiconductor layer with side surfaces exposed from both sides toward the center ((d) in FIG. 11), (v) removing the insulating film 8 ((e) in FIG. 11), (vi) forming the protective film 80 on the side surfaces of the plurality of LED structures ((f) in FIG. 11), (vii) exposing the lower electrode layer 40 by removing the protective film formed on the upper portion of the plurality of LED structures ((g) in FIG. 11), (viii) forming the arrangement inducing layer 70 on the lower electrode layer 40 ((h) in FIG. 11), and (x) separating the plurality of LED structures from the LED wafer to manufacture an ultra-thin LED assembly 100" including the plurality of ultra-thin LED devices 100". On the other hand, the above-described manufacturing method 2 can be performed by appropriately using a known method for manufacturing an LED device, and for a detailed description thereof, the application No. 2020-0050884 by the inventor of the present invention is incorporated herein by reference in its entirety, and in the present invention, detailed description of each step of the manufacturing method 2 is omitted.

In this case, the separation of the plurality of LED structures in step ix may be cutting using a cutting mechanism or detachment using an adhesive film.

On the other hand, as described above with reference to FIG. 8, the protective film 80' composed of the hole pushing film 81 and the electron pushing film 82 may be formed as a protective film for improving luminous efficiency, and the description thereof will be made with reference to FIG. 12.

Figures 11A, 11B, 11C, 11D, 11E, 11F, 11G, 11H, 11I:
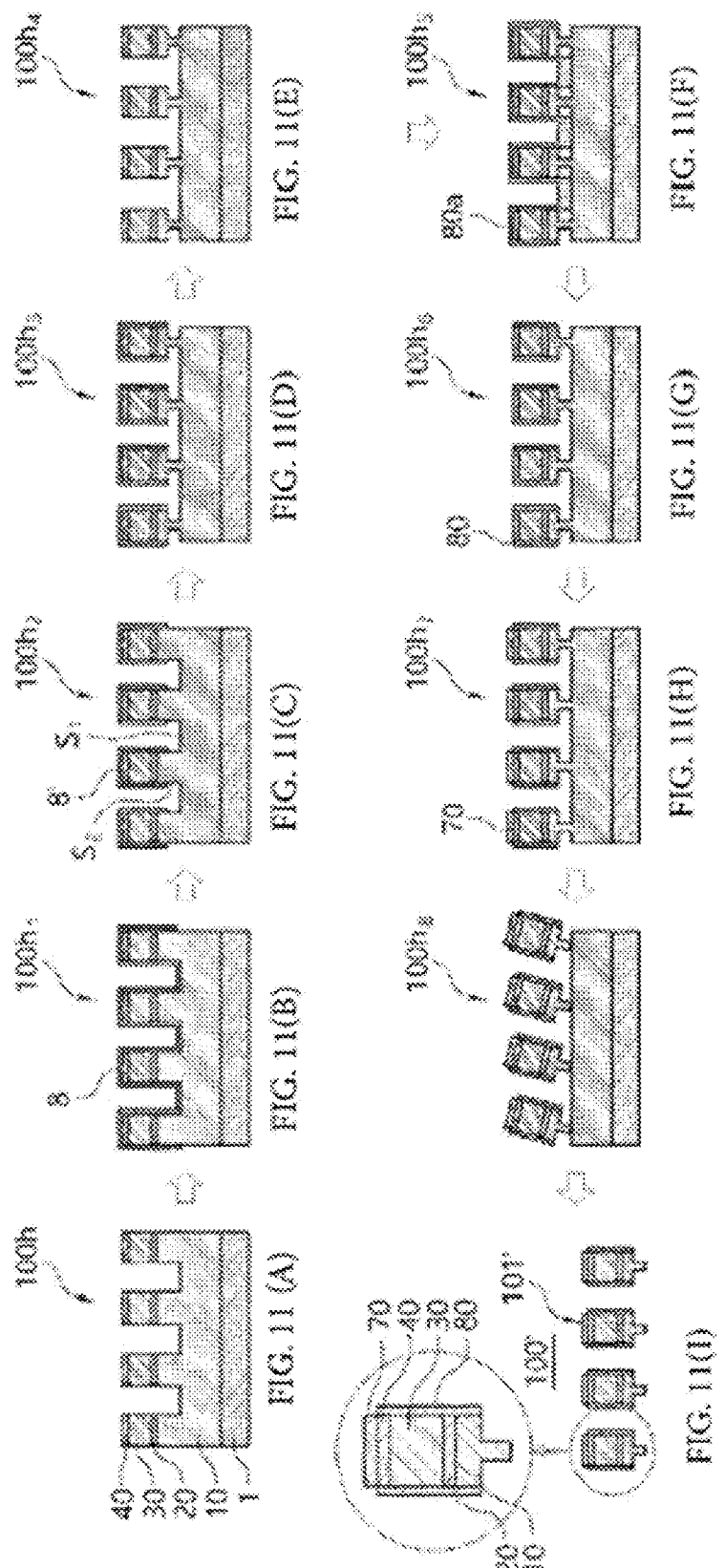
FIGS. 11(A) to 11(I) are schematic views of a device structure at different respective points in a method 2 for manufacturing an ultra-thin LED device (type 1) used in an embodiment of the present invention.
Figures 12A, 12B, 12C, 12D, 12E, 12F:
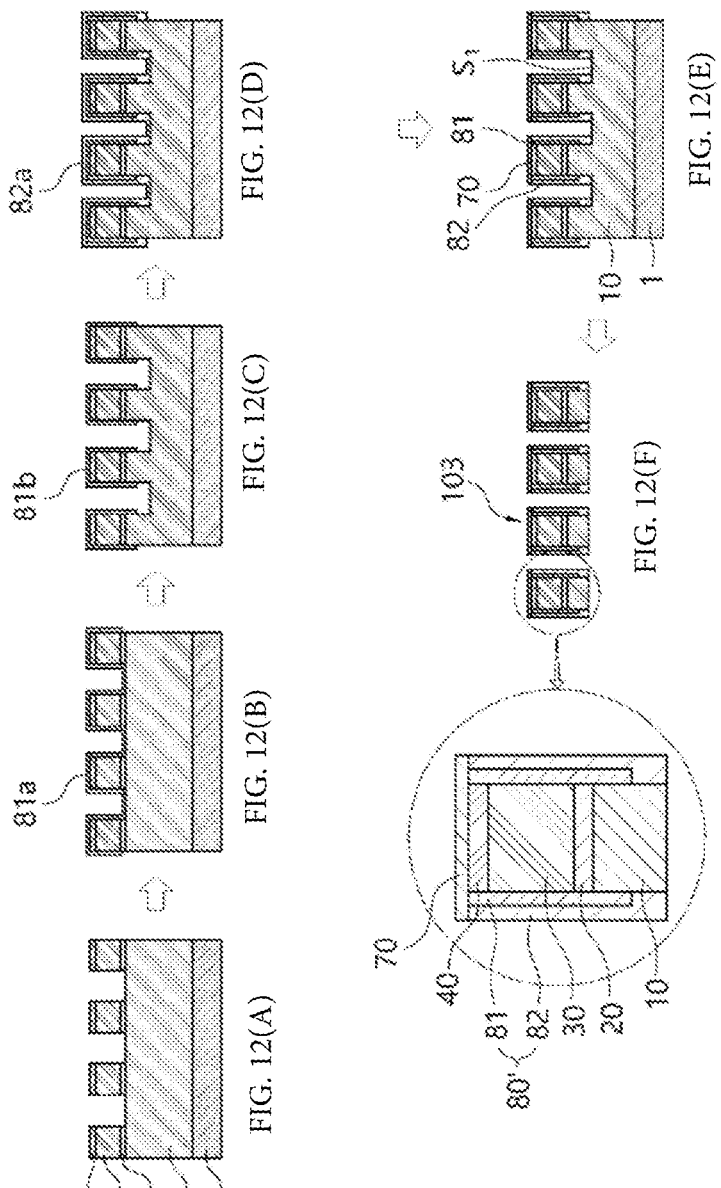
FIGS. 12(A) to 12(F) are schematic views of a device structure at different respective points in a method for manufacturing an ultra-thin LED device (type 1) used in an embodiment of the present invention.

The difference from the above-described FIGS. 9 to 11 is that, when etched in the vertical direction, the etching is not performed up to a portion of the first conductive semiconductor layer 10 which is an n-type semiconductor, but a first etching is performed only up to the second conductive semiconductor layer 30 or a portion of the photoactive layer 20 or up to photoactive layer 20 ((a) in FIG. 12); afterwards, a second etching is performed up to a partial thickness of the first conductive semiconductor layer 10 ((c) in FIG. 12), a film material is deposited, and the film material between the plurality of LED structures is removed twice ((b), (d), (e) in FIG. 12).

Specifically, when the LED wafer is etched in the vertical direction, without etching up to a portion of the first conductive semiconductor layer 10 that is an n-type semiconductor, the etching is primarily performed up to the second conductive semiconductor layer 30, up to the second conductive semiconductor layer 30 and a portion of the photoactive layer 20 or up to the photoactive layer 20 ((a) in FIG. 12). After depositing the hole pushing film material 81a is deposited ((b) in FIG. 12), the process of removing the hole pushing film material formed between the LED structures is performed. After that, the first conductive semiconductor layer 10 is etched again to a predetermined thickness ((c) in FIG. 12), and then the electron pushing film material 82a is deposited on the LED structure on which the hole pushing film 81b is formed ((d) in FIG. 12). Then, a process of removing the electron pushing film material formed between the LED structures (S₁) ((e) in FIG. 12) may be performed again. Thereafter, the process of separating the LED structure in FIGS. 9 to 11 ((k) and subsequent process in FIG. 9, (d) and subsequent processes in FIG. 10), or the process of separating the LED structure in FIG. 11 ((d) and subsequent processes in FIG. 11) is performed to separate the ultra-thin LED device 103 from the LED wafer.

The ultra-thin LED devices 101, 102, 103 obtained through the above-described method may be implemented with an ink composition. The ink composition may further include a dispersion medium and other additives provided in a known inkjet ink composition, and the present invention is not particularly limited thereto. However, as described above, the ultra-thin LED devices 101, 102, 103 have the advantage of being able to maintain a dispersed state for a long time by delaying precipitation during ink formation through the ratio between the thickness and the length of long axis in a cross section perpendicular to the stacking direction satisfying the above-mentioned specific ratio. In addition, the concentration of the ultra-thin LED devices 101, 102, 103 dispersed in the ink composition and the viscosity of the ink composition may be designed to be suitable for an inkjet printing apparatus for printing the ink composition, and the present invention is not particularly limited thereto. In addition, the inkjet printing apparatus is an apparatus capable of printing the ink composition containing the ultra-thin LED device on the lower electrode, and may be an apparatus employing a known method such as a piezoelectric method or an electrostatic method, so that the present invention is not particularly limited to an inkjet printing apparatus and a specific method of printing on the lower electrode using this.

Next, as step 3 according to the present invention, processing on the lower electrodes 311, 312, for example, the step of assembling the ultra-thin LED devices 101, 102, 103 printed through an inkjet printing device by erecting the devices in the thickness direction on the lower electrodes 311, 312 may be performed.

The plurality of ultra-thin LED devices 101, 102, 103 dispersed in the ink composition may not all be positioned on the disposing area in the lower electrode where the ultra-thin LED devices are to be disposed after printing on the lower electrode. In addition, even if the ultra-thin LED devices 101, 102, 103 are positioned within the disposing area, all the ultra-thin LED devices may not be disposed upright on the lower electrode in the thickness direction.

Accordingly, as described above in the ultra-thin LED electrode assembly 1000, the arrangement inducing layer 70 for arranging the LED devices 101, 102, 103 upright in the thickness direction may be further included in one side of the ultra-thin LED devices 101, 102, 103 in the thickness direction or either one or both sides of the disposing area where the ultra-thin LED devices are to be disposed in the lower electrodes 311, 312.

Figure 13:
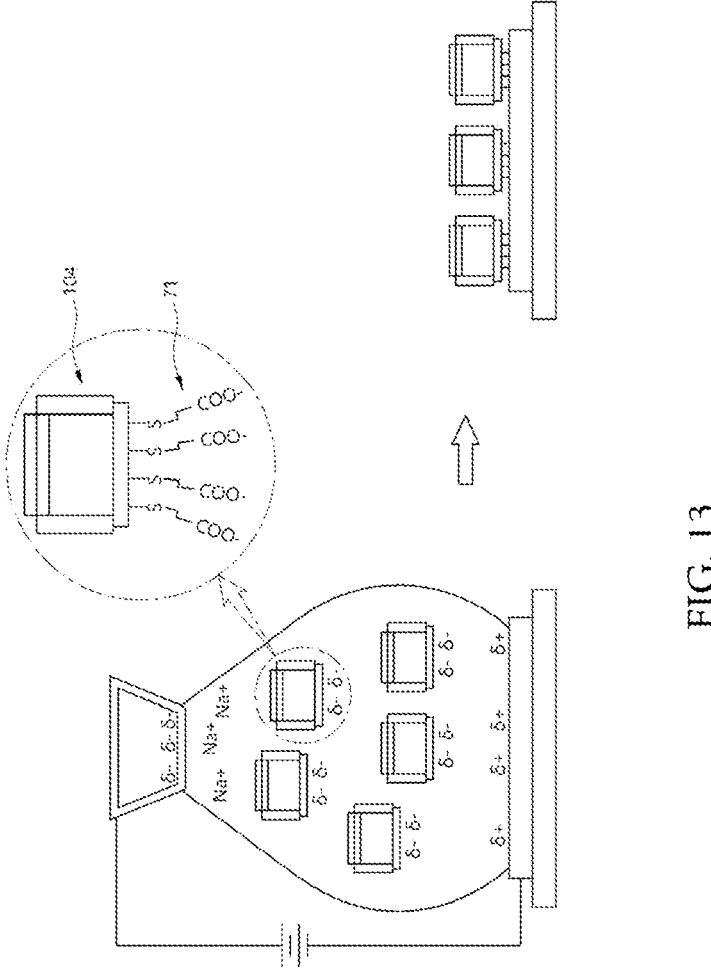
FIGS. 13 to 15 are schematic views illustrating several embodiments of a step of a method for manufacturing an ultra-thin LED electrode assembly using an ultra-thin LED device (type 2, micro-nanofin type) according to an embodiment of the present invention.

Specifically, with reference to FIG. 13, when the arrangement inducing layer 70 is the positive or negative charge layer 71, after printing the ink composition including the ultra-thin LED devices, or together with printing, or before printing, an electric field may be formed in a direction perpendicular to the main surface of the lower electrode 311 so that the ultra-thin LED device 104 is moved to the disposing area and disposed upright in the thickness direction through an electrophoresis method. In addition, when the charge layer provided in the ultra-thin LED device is a first charge layer having a positive or negative charge so that the ultra-thin LED devices are advantageously moved and erected in the disposing area, a second charge layer having a charge opposite to that of the first charge layer may be formed on the disposing area in the lower electrode. A second charge layer having a charge opposite to that of the charge layer may be provided. The thickness of the first charge layer and second charge layer may be, for example, 0.1 to 500 nm, but as long as the thickness is sufficient to carry charge, the present invention is not particularly limited thereto.

In addition, the strength of the electric field for moving and erecting the ultra-thin LED devices in the disposing region through the electrophoresis method can also be appropriately changed in consideration of the number and size of the ultra-thin LED devices in the ink composition, so the present invention is not particularly limited thereto.

Figure 14:
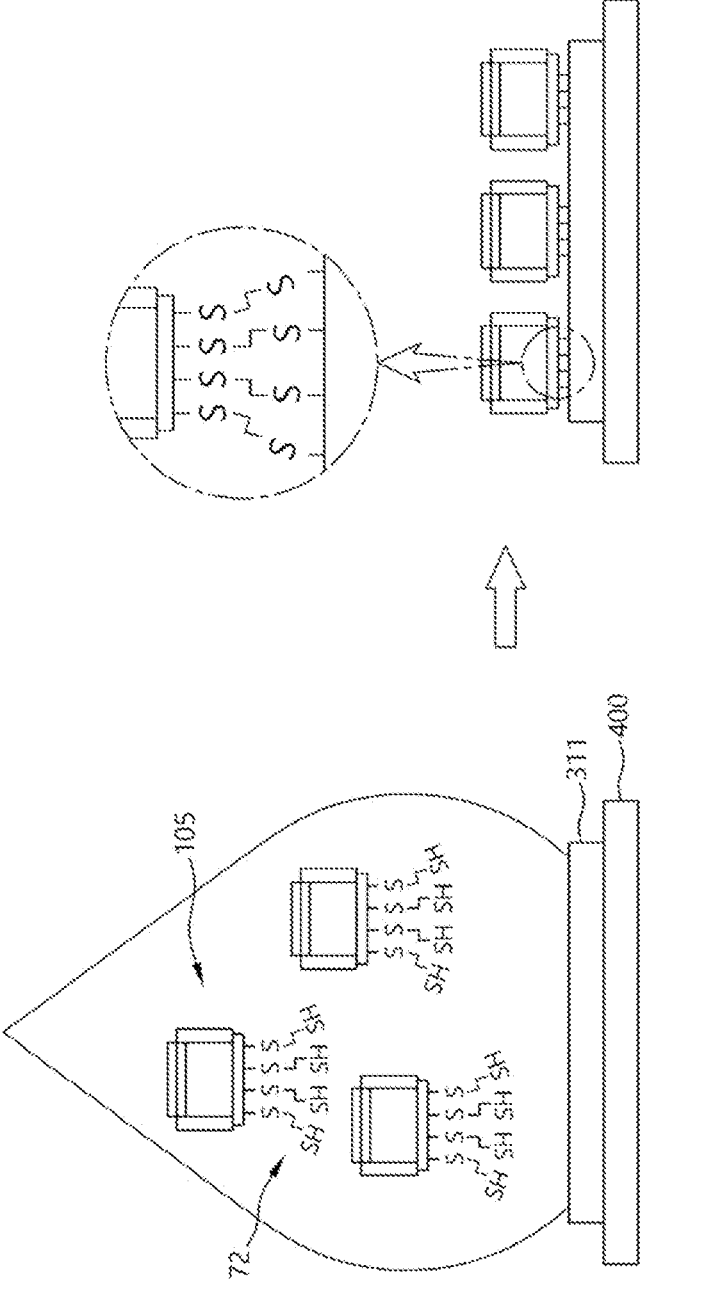

Alternatively, the case where the arrangement inducing layer 70 is the binding layer 72 is described with reference to FIG. 14. The ultra-thin LED device 105 may be erected and assembled on the disposing area through chemical bonding via the binding layer 72. In this case, the binding layer 72 may be provided on one side of the ultra-thin LED device 105 in the thickness direction and/or on the disposing area.

In addition, the binding layer may be formed such that, for example, a thiol group, an amine group, a carboxyl group, or a DNA single strand, etc., is exposed to the outside. Specifically, the binding layer may be formed through the compound such as aminoethanethiol, 1,2-ethanedithiol, 1,4-butanedithiol, 3-mercaptopropionic acid, a $NH_2$-terminated DNA single stranded. In addition, the chemical bond may be a covalent bond or a non-covalent bond, and for example, in the case of a binding layer in which a thiol group is exposed to the outside, it may be bounded to a metal lower electrode through a non-covalent bond. In addition, since the reaction rate is very slow when an amine group is combined with a carboxyl group to form an amide bond, (1-ethyl-3-(3-dimethylaminopropyl) carbodiimide (EDC) is added to form an active ester intermediate with a carboxyl group, and then an amide bond can be quickly formed by adding a primary amine, which is a strong nucleophile. In addition, in order to stabilize the ester intermediate using the EDC, sulfo N-hydroxysuccinimide (NHS) can be used so that the amide bond can proceed stably. In addition, the chemical bond may be a covalent bond or a non-covalent bond, and for example, in the case of a binding layer in which a thiol group is exposed to the outside, it may be bounded to a metal lower electrode through a non-covalent bond. In addition, the binding layer may include a first binding layer formed on the ultra-thin LED device and a second binding layer formed on the lower electrode side, and through complementary binding between a first linker in the first bonding layer and a second linker in the second bonding layer, the ultra-thin LED device can be erected and assembled on the lower electrode.

Figure 15:
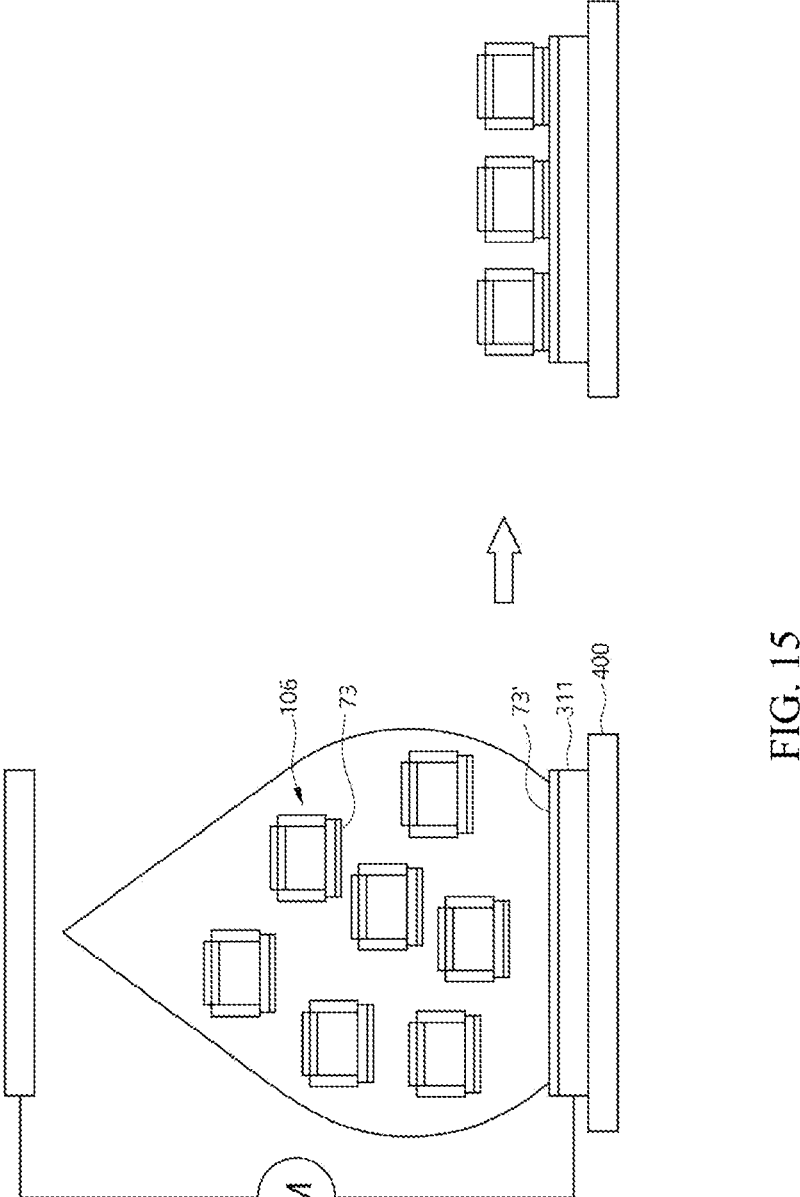

Alternatively, a case where the arrangement inducing layer 70 is the magnetic layer 73 is described with reference to FIG. 15. After printing the ink composition including the ultra-thin LED devices so that the ultra-thin LED device 106 moves to the disposing area through magnetic force and is erected and disposed in the thickness direction, or together with the printing or before printing, the magnetic field can be formed in a direction perpendicular to the main surface of the lower electrode 311. In addition, the magnetic layer may be formed on the disposing area within the lower electrode so that the ultra-thin LED device 106 can be moved to the disposing area and erected and disposed therein. The magnetic layer may be a paramagnetic material or a ferromagnetic material. In addition, the thickness of the magnetic layer 73 may be, for example, 0.1 to 500 nm, but the present invention is not particularly limited thereto.

Thereafter, the step of fixing and ohmically contacting the ultra-thin LED devices 104, 105, 106 erected and disposed on the lower electrodes 311, 312 to the lower electrodes 311, 312 may be further performed. The fixing and ohmic contact may be performed, for example, through a rapid thermal annealing (RTA) process on the interface between the lower electrode and the ultra-thin LED devices. Alternatively, a fixing layer having a low melting point is further provided on the disposing area in the lower electrodes 311, 312, and then the ultra-thin LED devices 104, 105, 106 are erected and disposed on the disposing area. Then, heat is applied to melt and solidify the fixed layer, so that the ultra-thin LED devices 104, 105, 106 can be firmly fixed on the lower electrodes 311, 312. The fixing layer may be, for example, a typical solder material used as an electrical and electronic material.

On the other hand, in order to improve electrical connectivity between the ultra-thin LED devices 104, 105, 106 and the lower electrodes 311, 312, after step 3, the step of forming a conducting metal layer 500 may be further performed. The conducting metal layer 500 may be prepared by patterning a line on which the conducting metal layer is to be deposited by applying a photolithography process using a photosensitive material and then depositing the conducting metal layer, or patterning the deposited metal layer and then etching. This process may be performed by appropriately employing a known method, and Korean Patent Application No. 10-2016-0181410 by the inventor of the present invention may be incorporated herein by reference.

In addition, the step of forming an insulating layer 600 to a predetermined thickness on the lower electrode line 310 for electrical insulation from the upper electrode line 320 to be formed in step 4 to be described later may be further performed. The insulating layer 600 may be formed through deposition of a known insulating material. For example, an insulating material such as $SiO_2$ or $SiN_x$ may be deposited through a PECVD method, or an insulating material such as AlN or GaN may be deposited through a MOCVD method. Alternatively, an insulating material such as $Al_2O$, $HfO_2$, or $ZrO_2$ may be deposited through an ALD method. On the other hand, the insulating layer 600 is preferably formed so as not to cover the upper surfaces of the ultra-thin LED devices 104, 105, 106 that are erected and assembled. To this end, the insulating layer may be formed through deposition to a thickness that does not cover the upper surfaces of the ultra-thin LED devices 104, 105, 106, or the insulating layer may be formed by depositing the insulating layer to a thickness that covers the upper surfaces of the ultra-thin LED device 104, 105, 106, and then dry etching until the upper surfaces of the ultra-thin LED device 104, 105, 106 are exposed.

Next, as step 4 according to the present invention, the step of forming the upper electrode line 320 including the upper electrodes 321, 322 so as to be electrically connected to the opposite side opposite to one side of the ultra-thin LED devices 104, 105, 106 electrically connected to the lower electrodes 311, 312 is performed. The upper electrode line 320 may be implemented by depositing an electrode material after patterning an electrode line using known photolithography or by depositing the electrode material and then dry and/or wet etching. In this case, the electrode material may be an electrode material commonly employed as an electrode of an electric/electronic material, and the present invention is not particularly limited thereto.

Next, a preferred embodiment of a micro-nanofin ultra-thin LED electrode device and an LED electrode assembly using the same will be described.

[Type 2 (Micro-Nanofin) Ultra-Thin LED Electrode Device and LED Electrode Assembly]

An LED electrode assembly manufactured by a second type ultra-thin LED device will be described with reference to FIGS. 16 and 17 as follows.

A micro-nanofin LED electrode assembly 1000 according to an embodiment of the present invention is implemented to include a lower electrode line 200 including a plurality of electrodes 211, 212, 213, 214 spaced in a horizontal direction at a predetermined interval, a plurality of micro-nanofin LED devices 107 disposed on the lower electrode line 200, and an upper electrode line 300 disposed in contact with the upper portions of the micro-nanofin LED devices 107.

First, before a detailed description of each configuration, the electrode lines for self-aligning the micro-nanofin LED device and emitting light will be described.

The micro-nanofin LED electrode assembly 1001 includes the upper electrode line 300 and the lower electrode line 200 disposed to face the upper and lower portions with the micro-nanofin LED devices 101 interposed therebetween. Since the upper electrode line 300 and the lower electrode line 200 are not arranged in a horizontal direction, an electrode design can be very simple and can be implemented more easily by avoiding the complicated electrode line of a conventional electrode assembly in which two types of electrodes implemented to have ultra-thin thickness and width are horizontally disposed to have micro or nano-scale spacing within a plane of a limited area.

Specifically, the conventional electrode assembly implemented by self-alignment of devices also uses the electrodes spaced apart in the horizontal direction as assembling electrodes to mount rod-type micro LED devices on the assembling electrodes. Here, the same electrode, that is, the assembling electrode, is used as a driving electrode as it is. On the other hand, the lower electrode line 200 provided in an embodiment of the present invention functions as the assembling electrode, but on the lower electrode line 200, only the surface of the first conductive semiconductor layer or the surface of the second conductive semiconductor layer is in contact, so that the micro-nanofin LED device 107 cannot be emitted using only the lower electrode line 200, which is distinguished from the conventional electrode assembly using electric field induction. This distinction causes a significant difference in the degree of freedom of electrode design and the easiness of electrode design.

In other words, when the same electrode is used as the assembling electrode and the driving electrode, the electrode structure should be able to mount the rod-type ultra-thin LED devices in as many numbers as possible in the plane of a limited area, and at the same time, it should be implemented to apply different voltages at intervals of micro-nano size. Thus, it was not easy to design or implement the electrode structure.

However, since the same type of power (e.g., (+) or (−) power) is applied to the lower electrode line 200 included in the present invention when driving, there is little risk of an electrical short circuit between the lower electrodes 211, 212, 213, 214 in the lower electrode line 200.

In addition, in the conventional art, both ends of each rod-type ultra-thin LED device had to be in contact with the adjacent electrodes in one-to-one correspondence so that light could be emitted without an electrical short circuit.

Accordingly, if each rod-type ultra-thin LED device is disposed across three or four adjacent electrodes, the photoactive layer of the rod-type ultra-thin LED device inevitably comes into contact with the electrode, resulting in a short circuit. Therefore, there was a difficulty in designing the electrode in consideration of preventing this. However, in the micro-nanofin LED device 107 included in the present invention, since the surface of the first conductive semiconductor layer or the second conductive semiconductor layer is in contact with the lower electrode line, even if the LED devices are disposed across several adjacent lower electrodes 211, 212, 213, 214, an electrical short circuit does not occur, and this has the advantage that the lower electrode line 200 can be designed more easily.

Figure 16:
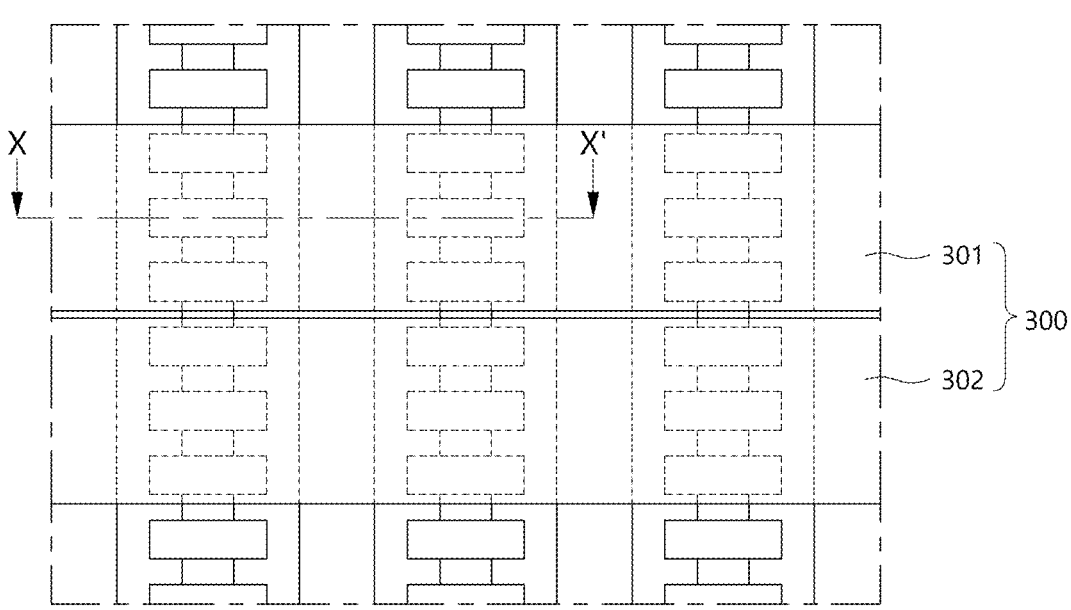
FIGS. 16 and 17 are views of a micro-nanofin LED electrode assembly according to an embodiment of the present invention.
Figure 17:
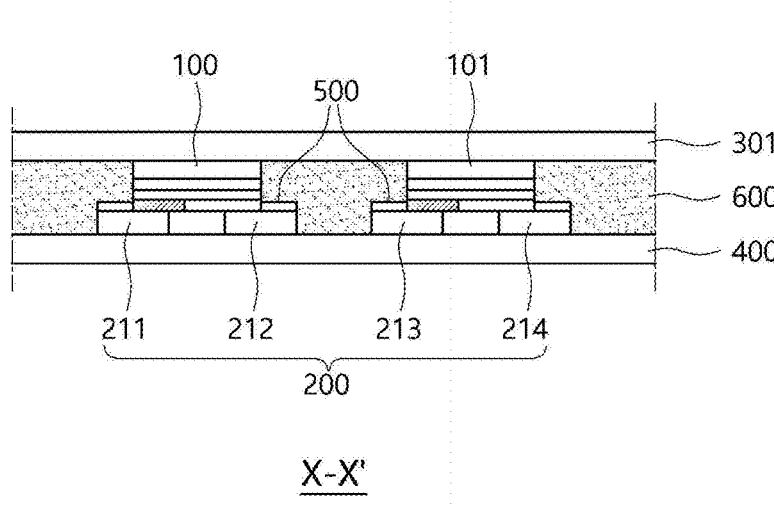

In addition, the upper electrode line 300 is arranged as shown in FIGS. 16 and 17 so that electrical contact is possible on the upper surfaces of the micro-nanofin LED devices 107, so the design or implementation of the electrode is very easy. In particular, although FIG. 16 shows that the upper electrode line 300 is implemented by dividing it into the first upper electrode 301 and the second upper electrode 302, it may also be implemented so that the upper surfaces of all the micro-nanofin LED devices disposed are in contact with one upper electrode. Therefore, there is an advantage that the electrode can be very simplified compared to the conventional art.

The lower electrode line 200 is an assembling electrode for self-aligning the micro-nanofin LED devices 107 so that the upper surfaces or lower surfaces of the micro-nanofin LED devices 107 in the thickness direction are in contact, and at the same time, it may function as one of the driving electrodes provided to emit light of the micro-nanofin LED devices 107 together with the upper electrode line 300 to be described later.

In addition, the lower electrode line 200 is implemented to include a plurality of lower electrodes 211, 212, 213, 214 spaced apart in the horizontal direction at a predetermined interval. The number and interval of the lower electrodes 211, 212, 213, 214 may be appropriately adjusted in consideration of the function as an assembling electrode and the length of the device.

In addition, as long as the plurality of lower electrodes 211, 212, 213, 214 included in the lower electrode line 200 is arranged to be spaced apart in the horizontal direction, there is no limitation on the specific electrode arrangement. For example, it may have a structure in which a plurality of electrodes is spaced apart by a predetermined interval in one direction and arranged side by side.

On the other hand, the distance between the adjacent electrodes 211, 212 may be smaller than the length of the micro-nanofin LED device 100, 107. If the distance between the two adjacent electrodes is equal to or wider than the length of the micro-nanofin LED device, the micro-nanofin LED device may be self-aligned in a form sandwiched between two adjacent electrodes. This case is not preferable because there is a high possibility that an electrical short circuit may occur due to contact between the electrode and the photoactive layer exposed on the side surface of the micro-nanofin LED device.

In addition, when the upper electrode line 300 is designed to be in electrical contact with the upper portion of the micro-nanofin LED device 107 mounted on the lower electrode line 200, there is no limitation on the number, arrangement, shape, or the like. However, as shown in FIG. 16, if the lower electrode line 200 is arranged side by side in one direction, the upper electrode line 300 may be arranged so as to be perpendicular to the one direction, and such an electrode arrangement has been widely used in displays and the like in the related art, and there is an advantage in that the electrode arrangement and control technology of the conventional display field can be used as it is.

Meanwhile, in FIG. 16, only the first upper electrode 301 and the second upper electrode 302 are shown so that the upper electrode line 300 including them only covers some devices, but this is simplified for ease of explanation. It should be noted that there is an additional upper electrode, not shown, disposed on the upper portion of the micro-nanofin LED device.

The lower electrode line 200 and the upper electrode line 300 may have the material, shape, width, and thickness of an electrode used in a typical LED electrode assembly, and may be manufactured using a known method, so the present invention does not specifically limit the material, shape, width, and thickness of an electrode. For example, the electrode may be aluminum, chromium, gold, silver, copper, graphene, ITO, AZO, or an alloy thereof, and have a width of 2 to 50 μm, a thickness of 0.1 to 100 μm, but may be appropriately changed in consideration of the size and the like of the desired LED electrode assembly.

Next, the micro-nanofin LED device 107 disposed between the above-described lower electrode line 200 and the upper electrode line 300 will be described.

Figure 18:
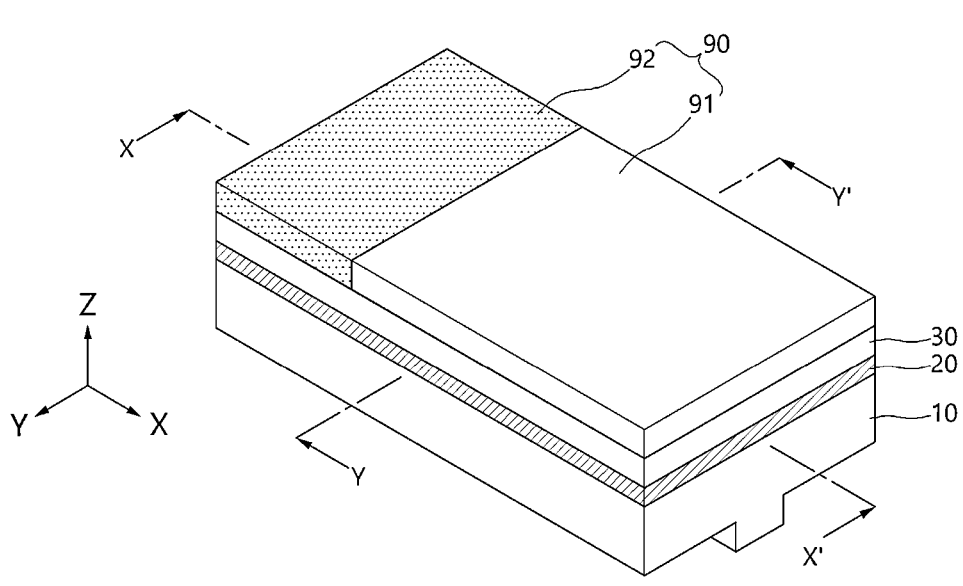
FIGS. 18 to 20 are a perspective view of a micro-nanofin LED device included in an embodiment of the present invention, a cross-sectional view taken along the line X-X' of FIG. 18, and a cross-sectional view taken along the line Y-Y' of FIG. 18.
Figure 19:
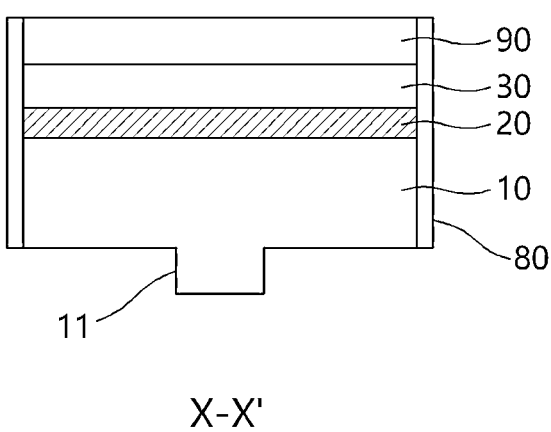
Figure 20:
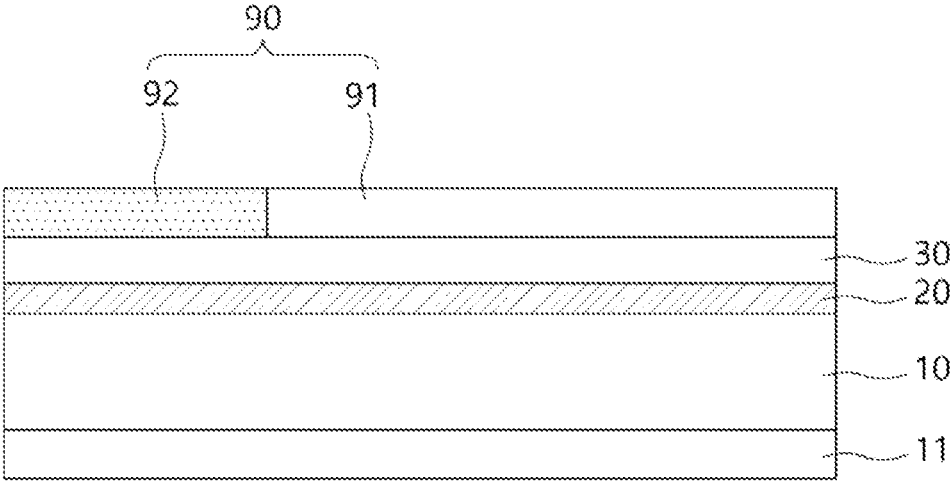

With reference to FIGS. 18 to 20, based on the mutually perpendicular X, Y, and Z axes, if the X-axis direction is a length, the Y-axis direction is a width, and the Z-axis direction is a thickness, the micro-nanofin LED device 107 according to an embodiment of the present invention is a rod type device in which the length is a long axis, the thickness is a short axis, and the length is greater than the thickness, and is a stacked device in which the first conductive semiconductor layer 10, the photoactive layer 20, the second conductive semiconductor layer 30, and a polarization inducing layer 90 are sequentially stacked.

More specifically, the micro-nanofin LED device 107 has a predetermined shape on an X-Y plane consisting of a length and a width, a direction perpendicular to the plane becomes a thickness direction, and each layer is stacked in the thickness direction. The micro-nanofin LED device having such a structure has an advantage in that it can secure a wide emitting area due to a plane having a length and a width even if the thickness of the photoactive layer 20 in the exposed portion on the side surface of the device is thin. In addition, due to this, the emitting area of the micro-nanofin LED device 100 according to an embodiment of the present invention may have a wide emitting area exceeding twice the longitudinal cross sectional area of the micro-nanofin LED device. Here, the longitudinal cross section is a cross-section parallel to the longitudinal X-axis direction, and in the case of a device having a constant width, it may be the X-Y plane.

Figure 21A:
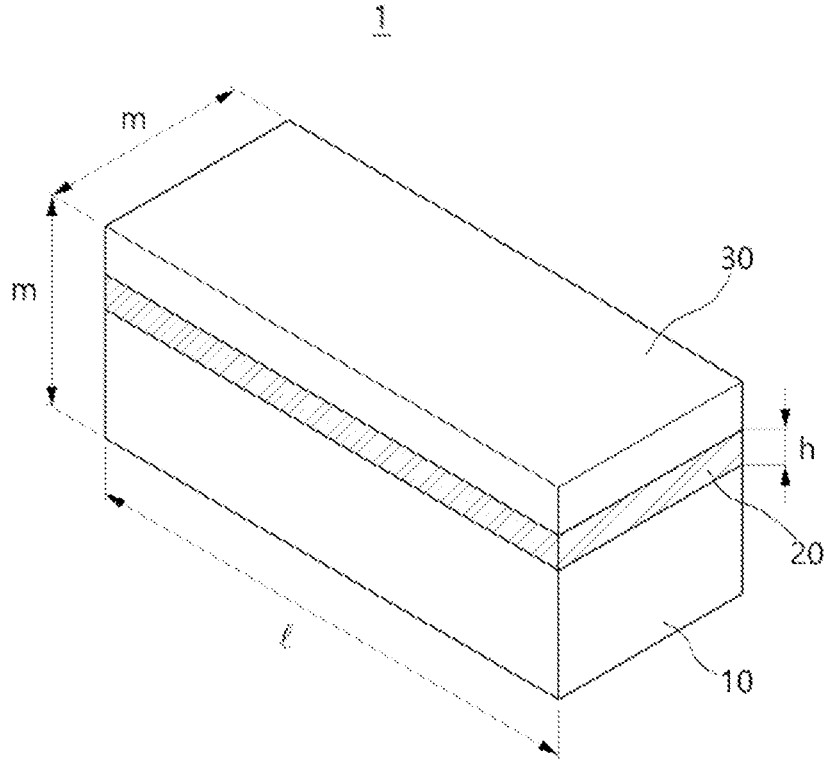
FIGS. 21A and 21B are a schematic view of a first rod-type device in which a first conductive semiconductor layer, a photoactive layer, and a second conductive semiconductor layer are stacked in a thickness direction, respectively, and a schematic view of a second rod-type device in which a first conductive semiconductor layer, a photoactive layer, and a second conductive semiconductor layer are stacked in a longitudinal direction, respectively.
Figure 21B:
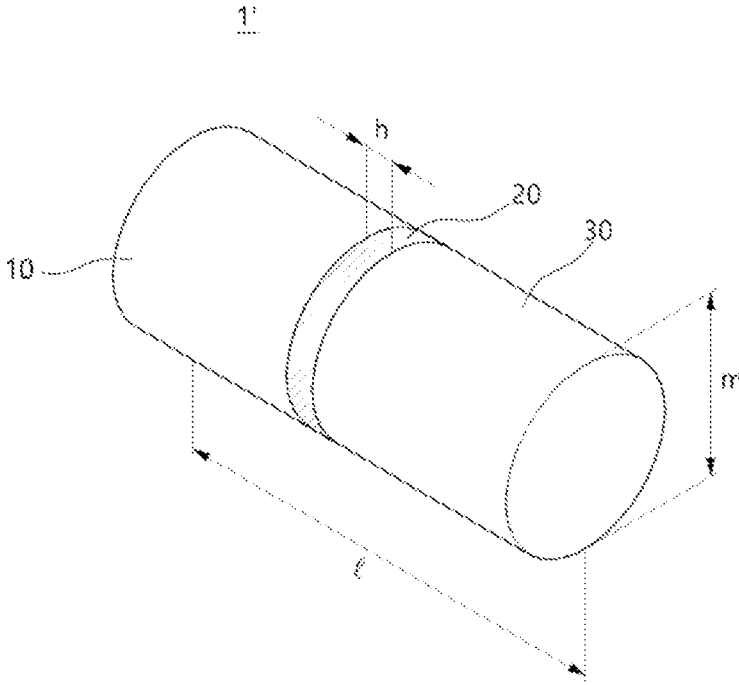

Specifically, with reference to FIGS. 21a and 21b, both a first rod-type device 1 shown in FIG. 21a and a second rod-type device 1' shown in FIG. 21b are rod type devices having a structure in which the first conductive semiconductor layer 10, the photoactive layer 20, and the second conductive semiconductor layer 30 are stacked, the length (l) and the thickness (m) are the same, and the thickness (h) of the photoactive layer is also the same. However, in the first rod-shaped device 1, the first conductive semiconductor layer 10, the photoactive layer 20, and the second conductive semiconductor layer 30 are stacked in the thickness direction, whereas in the second rod-type device 1', the respective layers are stacked in the longitudinal direction.

However, there is a big difference between the two devices 1, 1' in the emitting area. For example, assuming that the photoactive layer 3 has the length (l) of 4500 nm, the thickness (m) of 600 nm, and the thickness (h) of 100 nm, the ratio of the surface area, corresponding to an emitting area, of the photoactive layer 3 of the first rod type device 1 to the surface area of the photoactive layer 3 of the second rod type device 1' is 6.92 μm$^2$: 0.6597 μm$^2$, Thus, the emitting area of the micro-nanofin LED device 1 is 9.84 times larger than that of the device 1'. In addition, with respect to the ratio of the surface area of the photoactive layer 20 exposed to the outside to the emitting area of the total photoactive layers, the first rod type device 1 and the second rod type device 1' are similar to each other. However, since the absolute value of the increased surface area of the unexposed portion of the photoactive layer 20 is much larger, the effect of the exposed surface area on excitons is much reduced. Thus, since in relation to the effect of surface defects on excitons, the micro-nanofin LED device 1 is much smaller than the horizontally arrayed rod type device 1', the luminous efficiency and luminance of the micro-nanofin LED device 1 are superior to those of the horizontally arrayed rod type device 1'. In addition, in the case of the second rod-type device 1', a wafer on which the conductive semiconductor layer and the photoactive layer are stacked in the thickness direction is etched in the thickness direction. As a result, the long length of the device corresponds to the thickness of the wafer. In order to increase the length of the device, an increase in the etched depth is unavoidable. The greater the etched depth, the higher the possibility of occurrence of defects on the device surface. As a result, the second rod-type device 1' has a greater possibility of surface defects even though the area of the exposed photoactive layer is smaller than that of the first rod-type device 1. Thus, in consideration of the decrease in luminous efficiency due to the increase in the possibility of surface defects, ultimately the first rod-type device 1 can be significantly superior in luminous efficiency and luminance.

Furthermore, the moving distance of the holes injected from any one of the first conductive semiconductor layer 10 and the second conductive semiconductor layer 30 and the electrons injected from the other is shorter in the first rod-type device 1, compared to the second rod-type device 1'. Therefore, the probability of electrons and/or holes being captured by defects on the wall during electron and/or hole movement decreases, thereby minimizing luminescence loss, and emission loss due to electron-hole velocity imbalance. In addition, in the case of the second rod-type device 1', since a strong optical path behavior occurs due to the circular rod-shaped structure, the path of light generated by electron-holes resonates in the longitudinal direction, so that light is emitted from both ends in the longitudinal direction. Thus, when the device is disposed lying down, the front luminous efficiency is not good due to the strong side luminous profile. On the other hand, in the case of the first rod-type device 1, light is emitted from the upper surface and the lower surface, so there is an advantage of expressing excellent front luminous efficiency.

In the micro-nanofin LED device 107 of the present invention, the conductive semiconductor layers 10, 30 and the photoactive layer 20 are stacked in the thickness direction like in the first rod-type device 1 described above, and a length is greater than a thickness. Therefore, the device is advantageous to minimize or prevent a decrease in luminous efficiency due to defects even if the area of the exposed photoactive layer 20 is slightly increased, at the same time having a more improved light emitting area. This is because the device 107 has a rod type having a thickness smaller than the length, so that when the etch depth is shallow, the possibility of occurrence of defects on the exposed surface of the photoactive layer 20 can be reduced.

Although the plane is shown as a rectangle in FIG. 18, it is not limited thereto, and it should be noted that it can be employed without limitation, from a general rectangular shape such as a rhombus, a parallelogram, and a trapezoid to an oval.

The micro-nanofin LED device 107 according to an embodiment of the present invention has a size of micro or nano units in length and width. For example, the device may have a length of 100 to 5000 nm, and a width of 100 to 3000 nm. In addition, the thickness may be 100 to 3000 nm. The standard of the length and width may be different depending on the shape of the plane. For example, if the plane is a rhombus or a parallelogram, one of the two diagonals may be the length and the other may be the width. In the case of a trapezoid, the longer of height, upper and lower sides may be the length, and the shorter one perpendicular to the longer one may be the width. Alternatively, when the shape of the plane is an ellipse, the long axis of the ellipse may be the length and the short axis may be the width.

In this case, the ratio of the thickness and length of the micro-nanofin LED device 100 may be greater than 1:3, more preferably, greater than 1:6, and through this, the device may be more easily self-aligned on the lower electrode through an electric field. If the ratio of the thickness and length of the micro-nanofin LED device 100 is reduced to less than 1:3, it may be difficult to self-align the device on the electrode through an electric field, and the device is not fixed on the lower electrode. Accordingly, there is a risk of causing short circuiting of electrical contacts caused by a process defect. However, the ratio of the thickness and the length may be 1:15 or less, and through this, it may be advantageous to achieve the object of the present invention, such as optimization of the torque to cause self-alignment through an electric field.

In addition, the ratio of the width and the length in the plane may also be greater than 1:3, more preferably, 1:6 or more, and through this, self-alignment on the lower electrode can be more easily achieved through an electric field. However, the ratio of the width and the length may be 1:15 or less, which may be advantageous for optimization of the torque to cause self-alignment through the electric field.

In addition, the width of the micro-nanofin LED device 107 may be greater than or equal to the thickness. Through this, when the micro-nanofin LED device is aligned on the lower electrode line using an electric field, there is an advantage that side-lying alignment is minimized or prevented. If the micro-nanofin LED device is aligned while lying on its side, even if alignment and mounting in which one end and the other end contact the two adjacent lower electrodes (211/212, 213/214), respectively, are achieved, there is a risk that the device may not emit light due to an electrical short circuit that occurs as the photoactive layer in the exposed side surface of the device comes into contact with the electrode.

In addition, the micro-nanofin LED device 107 may be a device having different sizes at both ends in the longitudinal direction, for example, a rod-type device having a rectangular plane of an isosceles trapezoid whose length, which is the height, is greater than the top and bottom sides. Depending on the difference in length between the top and bottom sides, a difference between the amounts of positive and negative charges accumulated at both ends in the longitudinal direction of the device may occur as a result. Through this, the self-alignment by the electric field can be easily occurred.

In addition, on the lower surface of the first conductive semiconductor layer 10 of the micro-nanofin LED device 107, a protrusion 11 having a predetermined width and thickness may be formed in the longitudinal direction of the device, or a protrusion may not be formed.

The protrusion 11 will be described in detail in the description of the manufacturing method to be described later, but the protrusion may be formed as a result of etching the wafer in the thickness direction and then horizontally etching the etched LED portion from both sides of the lower portion of the etched LED portion to the central, inward in order to remove the etched LED portion from the wafer. The protrusion 11 may help to improve the extraction function of the front emission of the micro-nanofin LED device. In addition, when the micro-nanofin LED device is self-aligned on the lower electrode line, the protrusion 11 may help to control the alignment so that the polarization inducing layer 90, which is opposite to one surface of the device on which the protrusion 11 is formed, is positioned on the lower electrode line 200. Furthermore, the polarization inducing layer is positioned on the lower electrode line 200, and the upper electrode line 300 is formed on one surface of the device on which the protrusion 11 is formed. As the protrusion 11 increases the contact area with the upper electrode line 300 to be formed, it may be advantageous to improve the mechanical coupling force between the upper electrode line 300 and the micro-nanofin LED device 100.

In this case, the width of the protrusion 11 may be formed to be 50% or less, more preferably 30% or less of the width of the micro-nanofin LED device, and through this, the separation of the portion of the micro-nanofin LED device etched on the LED wafer may be more easily performed. If the protrusion is formed exceeding 50% of the width of the micro-nanofin LED device, it may not be easy to separate the portion of the micro-nanofin LED device etched on the LED wafer, and separation may occur at a portion that is not the intended portion. Therefore, mass productivity may be lowered, and there is a risk that the uniformity of the plurality of micro-nanofin LED devices may be lowered. Meanwhile, the width of the protrusion 11 may be formed to be 10% or more of the width of the micro-nanofin LED device. If the width of the protrusion is formed to be less than 10% of the width of the micro-nanofin LED device, separation of the device from the LED wafer may be easy, but during side etching (see (g) and (i) in FIG. 22) to be described later, there is a risk that even a portion of the first conductive semiconductor layer that should not be etched may be etched due to the excessive etching, and the effect according to the above-described protrusion 11 may not be exhibited. In addition, there is a risk that the device may be damaged by the wet etching solution, and the micro-nanofin LED device dispersed in the high-risk etching solution having a strong basic property needs to be cleaned separately from the wet etching solution. On the other hand, the thickness of the protrusion 11 may have a thickness of 10 to 30% of the thickness of the first conductive semiconductor layer. Through this, the first conductive semiconductor layer can be formed to have a desired thickness and quality, which may be more advantageous to express the effect by the protrusion 11. Here, the thickness of the first conductive semiconductor layer refers to a thickness based on the lower surface of the first conductive semiconductor layer on which the protrusion is not formed.

As a specific example, the protrusion 11 may have the width of 50 to 300 nm and the thickness of 50 to 900 nm.

Hereinafter, each layer included in the micro-nanofin LED device 107 will be described.

The micro-nanofin LED device includes the first conductive semiconductor layer 10 and the second conductive semiconductor layer 30. As the conductive semiconductor layer, a conductive semiconductor layer employed in general LED devices used for lighting, displays, and the like may be used without limitation. According to a preferred embodiment of the present invention, any one of the first conductive semiconductor layer 10 and the second conductive semiconductor layer 30 includes at least one n-type semiconductor layer, and the other may include at least one p-type semiconductor layer.

When the first conductive semiconductor layer 10 includes an n-type semiconductor layer, the n-type semiconductor layer may have at least one of semiconductor material of InAlGaN, GaN, AlGaN, InGaN, AlN, InN, and the like, which has a composition formula of $In_xAl_yGa_{1-x-y}N$ ($0 \leq x \leq 1$, $0 \leq y \leq 1$, $0 \leq x+y \leq 1$), and may be doped with a first conductive dopant (e.g., Si, Ge, Sn, etc.). According to a preferred embodiment of the present invention, the thickness of the first conductive semiconductor layer 10 may be 1.5 to 5 nm, but is not limited thereto.

When the second conductive semiconductor layer 30 includes a p-type semiconductor layer, the p-type semiconductor layer may have, for example, at least one of semiconductor material of InAlGaN, GaN, AlGaN, InGaN, AlN, InN, and the like, which has the composition formula of $In_xAl_yGa_{1-x-y}N$ ($0 \leq x \leq 1$, $0 \leq y \leq 1$, $0 \leq x+y \leq 1$), and may be doped with a second conductive dopant (e.g., Mg). According to a preferred embodiment of the present invention, the thickness of the second conductive semiconductor layer 30 may be 0.01 to 0.30 nm, but is not limited thereto.

According to an embodiment of the present invention, one of the first conductive semiconductor layer 10 and the second conductive semiconductor layer 30 includes a p-type GaN semiconductor layer, and the other includes an n-type GaN semiconductor layer. The p-type GaN semiconductor layer may have a thickness of 10 to 350 nm, and the n-type GaN semiconductor layer may have a thickness of 100 to 3000 nm, through which the moving distance of the holes injected into the p-type GaN semiconductor layer and the electrons injected into the n-type GaN semiconductor layer is shorter compared to the rod-type device in which the semiconductor layer and the photoactive layer are stacked in the longitudinal direction as shown in FIG. 21*b*. Due to this, the probability of electrons and/or holes being captured by defects on the wall during movement may be reduced, so emission loss is minimized, and it may also be advantageous to minimize emission loss due to electron-hole velocity imbalance.

Next, the photoactive layer 20 is formed on the first conductive semiconductor layer 10 and may have a single or multiple quantum well structure. As the photoactive layer 20, a photoactive layer included in a typical LED device used for lighting, display, and the like may be used without limitation. A clad layer (not shown) doped with a conductive dopant may be formed above and/or below the photoactive layer 20, and the clad layer doped with the conductive dopant may be implemented as an AlGaN layer or an InAlGaN layer. In addition, a material such as AlGaN or AlInGaN may be used as the photoactive layer 20. When an electric field is applied to the device, the electrons and holes that move from the conductive semiconductor layers each positioned above and below the photoactive layer to the photoactive layer generate electron-hole pairs in the photoactive layer 20, so emission is occurred. According to a preferred embodiment of the present invention, the thickness of the photoactive layer 20 may be 30 to 300 nm, but is not limited thereto.

Next, the polarization inducing layer 90 formed on the second conductive semiconductor layer 30 described above has both ends in the longitudinal direction of the device to have different electrical polarities from each other. Thus, this is the layer that facilitates self-alignment by an electric field, and at the same time, functions as an electrode layer due to increased conductivity when it is formed of a material such as a metal.

In addition, the polarization inducing layer 90 may have a first polarization inducing layer 91 disposed at one end along the longitudinal direction of the device, and a second polarization inducing layer 92 disposed at the other end thereof, and the first polarization inducing layer 91 and the second polarization inducing layer 92 may have different electrical polarities. For example, the first polarization inducing layer 91 may be ITO, and the second polarization inducing layer 92 may be a metal, a dielectric, or a semiconductor. In addition, the thickness of the polarization inducing layer 90 may be 50 to 500 nm, but is not limited thereto. The first polarization inducing layer 91 and the second polarization inducing layer 92 may be disposed in the same area by dividing the upper surface of the second conductive semiconductor layer 30 in two, but is not limited thereto. Either one of the first polarization inducing layer 91 and the second polarization inducing layer 92 may be disposed to have a larger area.

The first conductive semiconductor layer 10, the photoactive layer 20, the second conductive semiconductor layer 30, and the polarization inducing layer 90 described above may be included as minimum components of the LED device. The LED device may further include another phosphor layer, active layer, semiconductor layer, hole blocking layer and/or electrode layer on/below each of the layers.

Meanwhile, according to an embodiment of the present invention, the protective film 80 formed on the side surface of the micro-nano-fin LED device to cover the exposed surface of the photoactive layer 20 may be further included. The protective film 80 is a film for protecting the exposed surface of the photoactive layer 20, and covers at least all of the exposed surface of the photoactive layer 20, for example, both side surfaces, front surface and rear surface of the micro-nanofin LED device. The protective film 80 may include at least one of silicon nitride ($Si_3N_4$), silicon dioxide ($SiO_2$), aluminum oxide ($Al_2O_3$), hafnium oxide ($HfO_2$), zirconium oxide ($ZrO_2$), yttrium oxide ($Y_2O_3$), titanium dioxide ($TiO_2$), aluminum nitride (AlN) and gallium nitride (GaN). More preferably, the protective film 80 may be made of the above component, but may be transparent, but is not limited thereto. According to a preferred embodiment of the present invention, the thickness of the protective film 80 may be 5 nm to 100 nm, but is not limited thereto.

The above-described micro-nanofin LED device 107 may be manufactured by a manufacturing method described later, but is not limited thereto. Specifically, the micro-nanofin LED device may be manufactured by a process including the steps of (A) preparing an LED wafer in which a first conductive semiconductor layer, a photoactive layer, and a second conductive semiconductor layer are sequentially stacked on a substrate; (B) forming a polarization inducing layer patterned so that areas having different electrical polarities are adjacent to each other on the second conductive semiconductor layer of the LED wafer; (C) forming a plurality of micro-nanofin LED pillars by etching the LED wafer in the thickness direction so that each device has a plane having a nano or micro-sized length and width, and has a thickness perpendicular to the plane smaller than the length; and (D) separating the plurality of micro-nanofin LED pillars from the substrate.

Figures 22, 22A, 22B, 22C, 22D, 22E, 22F, 22G, 22H, 22I, 22J, 22K, 22L, 22M:
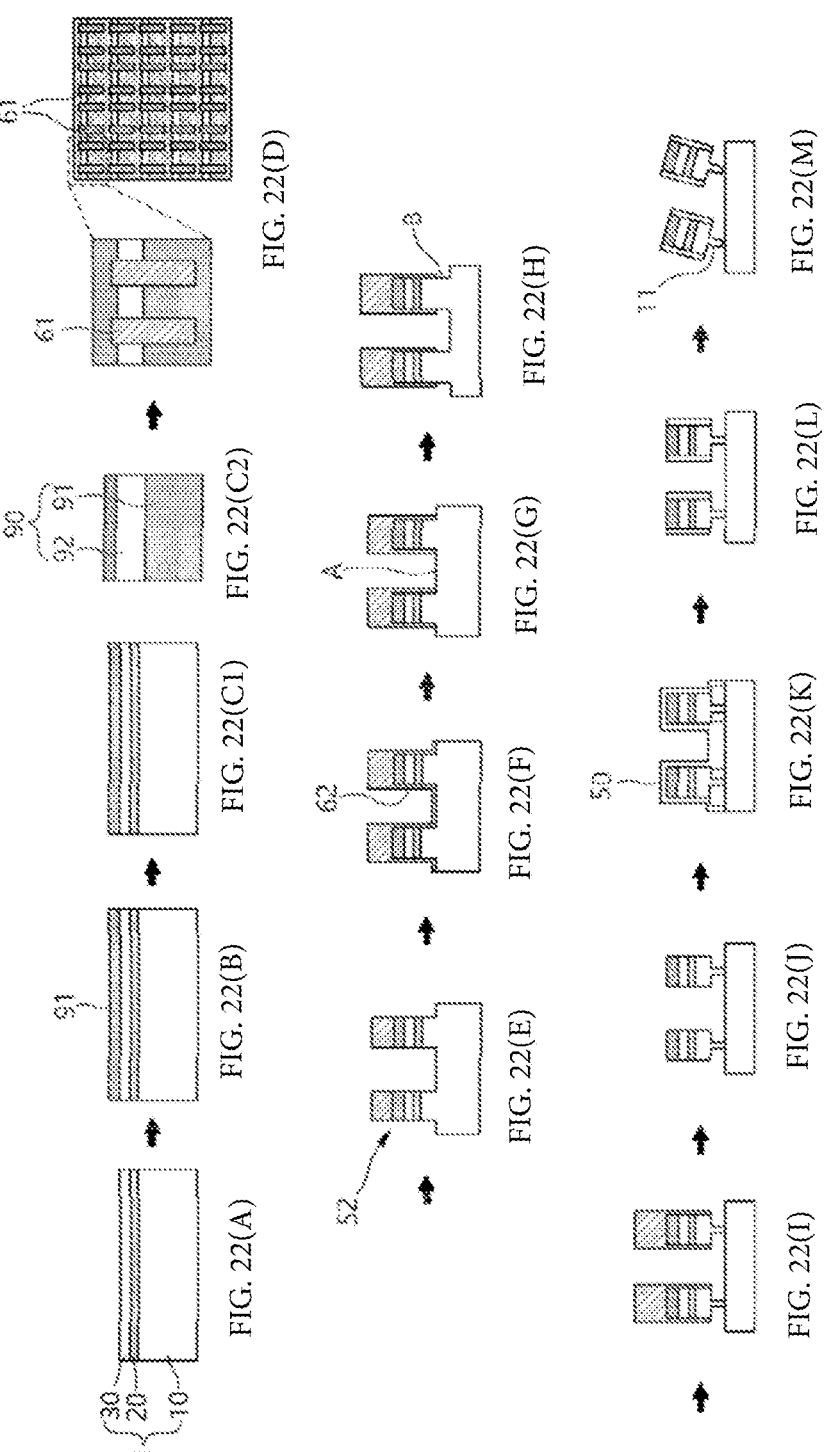
FIGS. 22(A) to 22(M) are schematic views of a device structure at different respective points in a manufacturing process of a micro-nanofin LED device included in an embodiment of the present invention.

With reference to FIG. 22, first, as step A of the present invention, the step of preparing the LED wafer 61 in which the first conductive semiconductor layer 10, the photoactive layer 20, and the second conductive semiconductor layer 30 are sequentially formed on a substrate (not shown) is performed.

Since the description of each layer provided in the LED wafer 51 is the same as that described above, a detailed description thereof will be omitted, and will be mainly described with reference to parts not described.

First, the thickness of the first conductive semiconductor 10 in the LED wafer 51 may be thicker than the thickness of the first conductive semiconductor layer 10 in the aforementioned micro-nanofin LED device 100. In addition, each layer in the LED wafer 51 may have a c-plane crystal structure.

The LED wafer 51 may have undergone a cleaning process, and since a commonly employed wafer cleaning solution and cleaning process may be appropriately employed as for the cleaning process, the present invention is not particularly limited thereto. The cleaning solution may be, for example, isopropyl alcohol, acetone and hydrochloric acid, but is not limited thereto.

Next, as step B of the present invention, the step of forming the polarization inducing layer 90 on the second conductive semiconductor layer 30 of the LED wafer 51 is performed as shown in (b) and (c1)/(c2) in FIG. 22. The polarization inducing layer 90 may be specifically patterned so that the areas having different electrical polarities are adjacent to each other on the second conductive semiconductor layer of the LED wafer. More specifically, step B may be formed by including the steps of B-1) forming the first polarization inducing layer 91 on the second conductive semiconductor layer 30 as shown in (b) in FIG. 22, B-2) etching the polarization inducing layer 91 in the thickness direction along a predetermined pattern and B-3) forming a polarization inducing layer 92 on an etched intaglio portion, as in (c1) and (c2) in FIG. 22.

First, as step B-1), the step of forming the first polarization inducing layer 91 on the second conductive semiconductor layer 30 is performed. The first polarization inducing layer 91 may be a typical electrode layer formed on a semiconductor layer, and may be, for example, Cr, Ti, Ni, Au, ITO, or the like, and preferably may be ITO in terms of transparency. The first polarization inducing layer 91 may be formed through a commonly employed method of forming an electrode, and may be formed by, for example, deposition through sputtering. For example, when ITO is used, it may be deposited to a thickness of about 150 nm, and may be further subjected to a rapid thermal annealing process after the deposition process. For example, the first polarization layer may be treated at 600° C. for 10 minutes, for example, but it may be appropriately adjusted in consideration of the thickness, material, etc. of the first polarization induction 91, but the present invention is not particularly limited thereto.

Next, as step B-2), the step of etching the first polarization inducing layer 91 in a thickness direction along a predetermined pattern is performed. This step is the step of preparing a point at which the second polarization inducing layer 92 to be described later is to be formed, and the pattern may be formed taking into account the area ratio and arrangement of the first polarization inducing layer 91 and second polarization inducing layer 92. As an example, the pattern may be formed such that the first polarization inducing layer 91 and the second polarization inducing layer 92 are alternately arranged side by side as shown in (d) in FIG. 22. Since the pattern can be formed by appropriately applying a commonly employed photolithography method or nanoimprinting method, a detailed description thereof will be omitted in the present invention.

The etching may be performed by employing an appropriate known etching method in consideration of the selected material of the first polarization inducing layer 91. For example, when the first polarization inducing layer 91 is ITO, it may be etched through wet etching. In this case, the etched thickness may be etched up to the upper surface of the second conductive semiconductor layer 30, that is, all of the ITO may be etched in the thickness direction, but is not limited thereto. Specifically, only a portion of ITO is etched in the thickness direction, and the second polarization inducing layer 92 may be formed on the etched intaglio portion. In this case, it is noted that the upper layer of one end of the device may be formed in a two-layer structure in which the first polarization inducing layer 91, which is ITO, and the second polarization inducing layer 92 are stacked.

Next, as step B-3), the step of forming the second polarization inducing layer 92 on the etched intaglio portion may be performed. The second polarization inducing layer 92 is a material having a different electrical polarity from that of the selected first polarization inducing layer 91, and can have any material used in a typical LED without limitation. For example, this material may be a metal, a dielectric, or a semiconductor. and, specifically, it may be nickel or chromium. As a method for forming these, a known method such as vapor deposition may be appropriately employed depending on a material, and the present invention is not particularly limited thereto.

Next, as step C of the present invention, the step of forming a plurality of micro-nanofin LED pillars 52 by etching the LED wafer 51 in the thickness direction so that each device has a plane having a nano or micro-sized length and width, and has a thickness perpendicular to the plane smaller than the length is performed.

Specifically, step C may be performed by including the steps of 3-1) forming a mask pattern layer 61 on the upper surface of the polarization inducing layer 90 so that each device has a plane having a predetermined shape with a length and width of nano or micro size ((d) in FIG. 22), C-2) forming the plurality of micro-nanofin LED pillars 52 by etching the first conductive semiconductor layer 10 to a partial thickness in the thickness direction along the pattern ((e) in FIG. 22), C-3) forming an insulating film 62 to cover the exposed side surface of the micro-nanofin LED pillar 52 ((f) in FIG. 22), C-4) removing a portion of the insulating film 62 formed on the upper surface of the first conductive semiconductor layer 10 so that the upper surface (A in (f) in FIG. 22) of the first conductive semiconductor layer 10 between the micro-nanofin LED pillars 52 is exposed ((g) in FIG. 22), C-5) forming a portion (B in (h) in FIG. 22) of the first conductive semiconductor layer with the side surface exposed by a predetermined thickness below the first conductive semiconductor layer of the micro-nanofin LED pillar on which the insulating film 62 is formed by further etching the first conductive semiconductor layer 10 in the thickness direction through the exposed upper portion (Ain (g) in FIG. 22) of the first conductive semiconductor layer ((h) in FIG. 22), C-6) etching the portion (B in (h) in FIG. 22) of the first conductive semiconductor layer with side surfaces exposed from both sides toward the center ((i) in FIG. 22), and C-7) removing the mask pattern layer 61 disposed on the polarization inducing layer 90 and the insulating film 62 covering the side surface ((j) in FIG. 22).

First, as step C-1), the step of forming a mask pattern layer 61 on the upper surface of the polarization inducing layer 90 so that each device has a plane having a predetermined shape with a length and width of nano or micro size ((d) in FIG. 20).

The mask pattern layer 61 is a layer that is patterned to have a desired planar shape of the implemented LED device, and may be formed of a known method and material used for etching an LED wafer. The mask pattern layer 61 may be, for example, a SiO₂ hard mask pattern layer. Briefly, the mask pattern layer 61 may be formed by including the steps of forming an unpatterned SiO₂ hard mask layer on the polarization inducing layer 90, forming a metal layer on the SiO₂ hard mask layer, forming a predetermined pattern on the metal layer, etching the metal layer and the SiO₂ hard mask layer along the pattern, and removing the metal layer.

The mask layer is a layer from which the mask pattern layer 61 is derived. For example, SiO₂ may be formed through deposition. The mask layer may have a thickness of 0.5 to 3 μm, for example, 1.2 In addition, the metal layer may be, for example, an aluminum layer, and the aluminum layer may be formed through deposition. The predetermined pattern formed on the formed metal layer is for realizing the pattern of the mask pattern layer, and may be a pattern formed by a conventional method. For example, the pattern may be formed through photolithography using a photosensitive material or may be a pattern formed through a known nanoimprinting method, laser interference lithography, electron beam lithography, or the like. Thereafter, the metal layer and the SiO₂ hard mask layer are etched according to the formed pattern. For example, the metal layer may be etched using inductively coupled plasma (ICP), and the SiO₂ hard mask layer or the imprinted polymer layer may be etched using a dry etching method such as a reactive ion etching (RIE).

Next, a step of removing the metal layer, other photosensitive material layers, or the remaining polymer layer according to the imprint method, which is remained on the etched SiO₂ hard mask layer may be performed. The removing step may be performed through a conventional wet etching or dry etching method depending on the material, and detailed description thereof will be omitted in the present invention.

(d) in FIG. 22 is a plan view of the SiO₂ hard mask layer 61 patterned on the polarization inducing layer 90. In the subsequent step C-2), as shown in (e) in FIG. 22, the step of forming the plurality of micro-nanofin LED pillars 52 by etching a partial thickness of the first conductive semiconductor layer 10 in the thickness direction of the LED wafer 51 along the pattern may be performed. The etching may be performed through a conventional dry etching method such as ICP.

After that, in step C-3), as shown in (f) in FIG. 22, the step of forming the insulating film 62 to cover the exposed side surface of the micro-nanofin LED pillar 52 may be performed. The insulating film 62 coated on the side surface of the LED pillar 52 may be formed through vapor deposition, and the material thereof may be, for example, SiO₂, but is not limited thereto. The insulating film 62 functions as a side mask layer. Specifically, in order to separate the micro-nanofin LED pillar 52 as shown in (i) in FIG. 22, in the process of etching the portion (B) of the first conductive semiconductor layer, the insulating film 62 allows the side surface of the micro-nanofin LED pillar 52 to remain and prevents damage due to the etching process. The insulating film 62 may have a thickness of 100 to 600 nm, but is not limited thereto.

Next, as step C-4), as shown in (g) in FIG. 22, the step of removing a portion of the insulating film 62 formed on the upper surface of the first conductive semiconductor layer 10 so that the upper surface (A in (g) in FIG. 22) of the first conductive semiconductor layer 10 between the adjacent micro-nanofin LED pillars 52 is exposed may be performed. The removal of the insulating film 62 may be performed through an appropriate etching method in consideration of the material, and the insulating film 62 made of SiO₂ may be removed through dry etching such as RIE.

Next, as step C-5), as shown in (h) of FIG. 22, the step of forming the portion (B in (h) in FIG. 22) of the first conductive semiconductor layer with the side surface exposed by a predetermined thickness below the first conductive semiconductor layer of the micro-nanofin LED pillar on which the insulating film 62 is formed by further etching the first conductive semiconductor layer 10 in the thickness direction through the exposed upper portion (A in (g) in FIG. 22) of the first conductive semiconductor layer is performed. As described above, the exposed portion (B) of the first conductive semiconductor layer 10 is a portion on which the side etching is performed in a direction horizontal to the substrate in a step to be described later. The process of further etching the first conductive semiconductor layer 10 in the thickness direction may be performed by, for example, a dry etching method such as ICP.

Thereafter, as step C-6), as shown in (i) in FIG. 22, the step of side etching the portion (B in (h) in FIG. 22) of the first conductive semiconductor layer with side surfaces exposed in a horizontal direction to the substrate may be performed. The side etching may be performed through wet etching, and for example, the wet etching may be performed at a temperature of 60 to 100° C. using a tetramethylammonium hydroxide (TMAH) solution.

Thereafter, after wet etching in the lateral direction is performed, as shown in (j) in FIG. 22, as step C-7), the step of removing the mask pattern layer 61 disposed on the polarization inducing layer 90 and the insulating film 62 covering the side surface may be performed. Both the material of the mask pattern layer 61 and the insulating film 62 disposed on the polarization inducing layer 90 may be SiO₂, and may be removed by wet etching. For example, the wet etching may be performed using a buffer oxide etchant (BOE).

According to an embodiment of the present invention, as a step E between steps C and D described above, as shown in (k) in FIG. 22, the step of forming the protective film 80 on the side surfaces of the plurality of micro-nanofin LED pillars may be further performed. The protective film 80 may be formed by, for example, deposition, and may have a thickness of 10 to 100 nm, for example, 90 nm, and may have a material, for example, alumina. When using alumina, an atomic layer deposition (ALD) method may be used as an example of the deposition. In addition, in order to form the deposited protective film 80 only on the side surfaces of the plurality of micro-nanofin LED pillars, the protective film 80 positioned on the remaining portions except for the side surfaces is removed by etching, for example, dry etching through ICP. Meanwhile, although (l) in FIG. 22 shows that the protective film 80 surrounds the entire side surface, it should be noted that the protective film 80 may not be formed on all or some of the remaining portions except for the photoactive layer on the side surface.

Next, as a step D according to the present invention, as shown in (m) in FIG. 22, the step of separating the plurality of micro-nanofin LED pillars 80 from the substrate is performed. The separation may be cut using a cutting mechanism or detachment using an adhesive film, and the present invention is not particularly limited thereto.

On the other hand, as shown in FIG. 17, the micro-nanofin LED device 107 may be disposed so that among the surfaces of the device where the respective layers are stacked in the thickness direction, one surface of the device on the polarization inducing layer is in contact with the adjacent two electrodes 211/212, 213/214 of the lower electrode line 200. The first conductive semiconductor layer 10, which is the surface opposite to one surface of the device in contact with the lower electrode line 200, may be in contact with the upper electrode line 300. In this case, due to the protrusion formed on one surface of the first conductive semiconductor layer 10, the polarization inducing layer 90 may be disposed to contact the lower electrode line 200 with a higher probability.

In addition, in the lower electrode line 200, a unit electrode area, that is, an area which can be independently driven by disposing the micro-nanofin LED device on the lower electrode line 200, and then disposing the upper electrode line 300 on the micro-nanofin LED device, may be preferably 1 $\mu m^2$ to 100 $cm^2$, and more preferably 10 $\mu m^2$ to 100 $mm^2$, but the unit electrode area is not limited to the above area.

According to an embodiment of the present invention, as shown in FIG. 17, a conducting metal layer 500 that connects the polarization inducing layer 90 of the micro-nanofin LED device 107 contacting the lower electrode line 200 and the lower electrode line 200 may be further included in order to reduce the contact resistance between the micro-nanofin LED devices 107 disposed on the lower electrode line 200. The conducting metal layer 500 may be a conducting metal layer such as silver, aluminum, or gold, and may be formed to have a thickness of, for example, about 10 nm.

In addition, an insulting layer 600 may be further included in a space between the first conductive semiconductor layer 10 corresponding to the upper surface of the self-aligned micro-nanofin LED device 107 on the lower electrode line 200 and the upper electrode line 300 in electrical contact with the layer 10. The insulating layer 600 prevents electrical contact between the two electrode lines 200, 300 facing vertically, and performs a function of more easily implementing the upper electrode line 300.

As the insulating layer 600, any material performing a general insulating function may be used without limitation. Preferably, it may be a transparent material, and for example, it may be a layer formed of an insulating material such as $SiN_x$, $Al_2O$, $HfO_2$, $ZrO_2$.

The micro-nanofin LED electrode assembly 1001 according to an embodiment of the present invention described above may be manufactured by a process including the steps of (1) injecting, on the lower electrode line 200 including the plurality of lower electrodes 211, 212, 213, 214 spaced apart in the horizontal direction at a predetermined interval, a solution containing the plurality of micro-nanofin LED devices 107 wherein each device is a rod type device having a plane having a length and width of nano or micro size and a thickness perpendicular to the plan smaller than the length, and in each device, the first conductive semiconductor layer 10, the photoactive layer 20, the second conductive semiconductor layer 30, and the polarization inducing layer 90 are sequentially stacked, (2) self-aligning the micro-nanofin LED devices 17 so that the first conductive semiconductor layers 10 or polarization inducing layers 90 of the micro-nanofin LED devices 107 in the solution are in contact with at least 17 adjacent lower electrodes 211/212, 213/214 by applying an assembling voltage to the lower electrode line 200, and (3) forming the upper electrode line 300 on the plurality of self-aligned micro-nanofin LED devices 107.

First, as step 1, the step of injecting the solution containing the plurality of micro-nanofin LED devices 107 on the lower electrode line 200 including the plurality of lower electrodes 211, 212, 213, and 214 spaced apart in the horizontal direction at a predetermined interval is performed.

The solution containing the plurality of micro-nanofin LED devices 107 may contain the plurality of micro-nanofin LED devices 107 and a solvent for dispersing and moving the plurality of micro-nanofin LED devices 107 to the electrode of the lower electrode line. In this case, the solution may be in the form of ink or paste, and the solution may be injected onto the lower electrode line 200 using an inkjet. On the other hand, although step 1 has been described as a case in which the device is put into a solution mixed with a solvent, the step also includes the case in which the device is first put on the lower electrode line, and then the solvent is added, which is consequently the same case as the solution is inserted.

The solvent may be at least one selected from the group consisting of acetone, water, alcohol, and toluene, and more preferably acetone. However, the type of solvent is not limited to the above description, and any solvent that can evaporate well without physically and chemically affecting the micro-nanofin LED device may be used without limitation. Preferably, the micro-nanofin LED devices may be added in an amount of 0.001 to 100 parts by weight based on 100 parts by weight of the solvent. If the amount is less than 0.001 parts by weight, the number of micro-nanofin LED devices connected to the lower electrode may be small, so it may be difficult to perform the normal function of the electrode assembly. In this case, there may be a problem that the solution must be added dropwise several times in order to overcome the problem. If the amount exceeds 100 parts by weight, there may be a problem that the alignment of individual micro-nanofin LED devices may be disturbed.

Next, as step 2, the step of self-aligning the micro-nanofin LED devices 17 so that the first conductive semiconductor layers 10 or polarization inducing layers 90 of the micro-nanofin LED devices 107 in the solution are in contact with at least 17 adjacent lower electrodes 211/212, 213/214 by applying an assembling voltage to the lower electrode line 200 is performed.

In step 2, charges are induced in the micro-nanofin LED devices by induction of the electric field formed by the potential difference between the lower electrodes 211/212, 213/214 adjacent to the micro-nanofin LED devices, and in the longitudinal direction of the micro-nanofin LED devices, the devices are self-aligned by inducing the devices to have different charges toward both ends with the center of the device as the center.

A power may be applied such that a potential difference is formed between any one of two adjacent lower electrodes among the plurality of lower electrodes of the lower electrode line, and the other, or between a first group consisting of two or more adjacent lower electrodes and a second group consisting of two or more adjacent lower electrodes adjacent to the first group. In this case, for the intensity, type, etc. of the applied assembling voltage, Korean Patent Application Nos. 10-2013-41080912, 10-2016-0092737, 10-2016-0073572, etc. by the inventor of the present invention will be incorporated by reference.

Next, as step 3 of the present invention, the step of forming the upper electrode line 300 on the plurality of self-aligned micro-nanofin LED devices 107 is performed. The upper electrode line 300 may be implemented by depositing an electrode material after patterning the electrode line using known photolithography, or by depositing the electrode material and then dry and/or wet etching. In this case, since the electrode material is the same as the electrode material of the lower electrode line described above, the description about the material will be omitted.

On the other hand, as step 4 between steps 2 and 3 described above, the step of forming the conducting metal layer 500 connecting the polarization inducing layer 90 of each micro-nanofin LED device 107 in contact with the lower electrode line 200 and the lower electrode line 200 and, as step 5, the step of forming the insulating layer 600 on the lower electrode line 200 such that the upper surfaces of the self-aligned micro-nanofin LED devices 107 are not covered may be further included.

The conducting metal layer 500 may be prepared by patterning a line on which the conducting metal layer is to be deposited by applying a photolithography process using a photosensitive material and then depositing the conducting metal layer, or patterning the deposited metal layer and then etching. This process may be performed by appropriately employing a known method, and Korean Patent Application No. 10-2016-0181410 by the inventor of the present invention may be incorporated herein by reference.

After forming the conducting metal layer 500, the step of forming the insulting layer 600 on the lower electrode line 200 such that the self-aligned micro-nanofin LED device 107 is not covered may be performed. The insulating layer 600 may be formed through deposition of a known insulating material. For example, an insulating material such as $SiO_2$ or $SiN_x$ may be deposited through a PECVD method, or an insulating material such as AlN or GaN may be deposited through a MOCVD method. Alternatively, an insulating material such as $Al_2O$, $HfO_2$, or $ZrO_2$ may be deposited through an ALD method. On the other hand, the insulating layer 600 is formed so as not to cover the self-aligned upper surfaces of the micro-nanofin LED devices 107. To this end, the insulating layer may be formed through deposition to a thickness that does not cover the upper surfaces, or the insulating layer may be formed by depositing the insulating layer to cover the upper surfaces, and then dry etching until the upper surfaces of the devices are exposed.

Hereinafter, the present invention will be described in more detail through examples, but the following examples are not intended to limit the scope of the present invention, which should be construed to aid understanding of the present invention.

EXAMPLES

Preparation Example 1: Preparation of First Type Ultra-Thin LED Device

A general LED wafer (Epistar) in which an undoped n-type III-nitride semiconductor layer, an n-type III-nitride semiconductor layer doped with Si (thickness of 4 μm), a photoactive layer (thickness of 0.45 μm) and a p-type III-nitride semiconductor layer (thickness of 0.05 μm) were sequentially stacked on a substrate was prepared.

After sequentially deposing ITO (thickness of 0.15 μm) as a lower electrode layer, $SiO_2$ (thickness of 1.2 μm) as a first mask layer, and Al (thickness of 0.2 μm) as a second mask layer on the prepared LED wafer, a SOG resin layer to which a pattern was transferred was transferred onto the second mask layer using a nanoimprint equipment.

Thereafter, the SOG resin layer was cured using RIE, and the residual resin portion of the resin layer was etched through RIE to form a resin pattern layer. After that, the second mask layer was etched using ICP according to the pattern, and the first mask layer was etched using ME. Thereafter, the lower electrode layer, the p-type III-nitride semiconductor layer, and the photoactive layer were etched using ICP, and then the doped n-type III-nitride semiconductor layer was etched to the thickness of 0.78 μm, and then KOH wet etching was performed to manufacture a LED wafer having a plurality of LED structures (diameter of 850 nm, height of 850 nm) in which the side surface of the etched doped n-type III-nitride semiconductor layer was perpendicular to the surface of layer.

Figure 23:
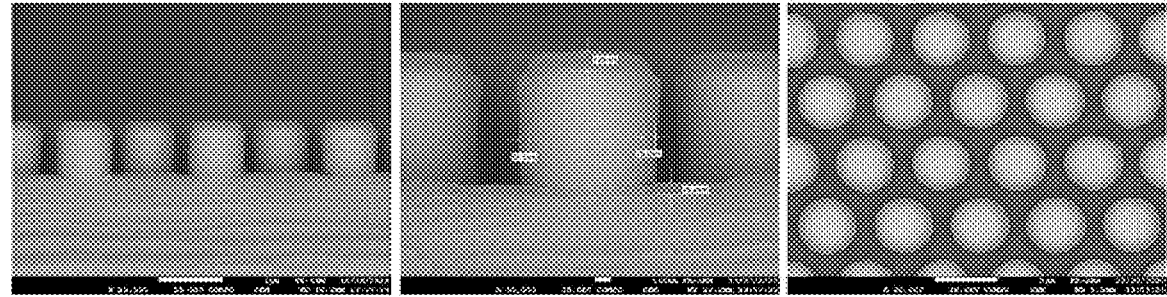
FIGS. 23 and 24 are SEM photographs at a specific step in a method for manufacturing an ultra-thin LED device (type 1) used in an embodiment of the present invention.

After that, a protective film material of $SiN_x$ was deposited on the LED wafer on which the plurality of LED structures was formed (see SEM photograph in FIG. 23, deposition thicknesses of 52.5 nm and 72.5 nm based on the side surface of the LED structure), and then the protective film material formed between the plurality of LED structures was removed through reactive ion etcher to expose the upper surface ($S_1$) of the first portion (a) of the doped n-type III-nitride semiconductor layer.

Figure 24:
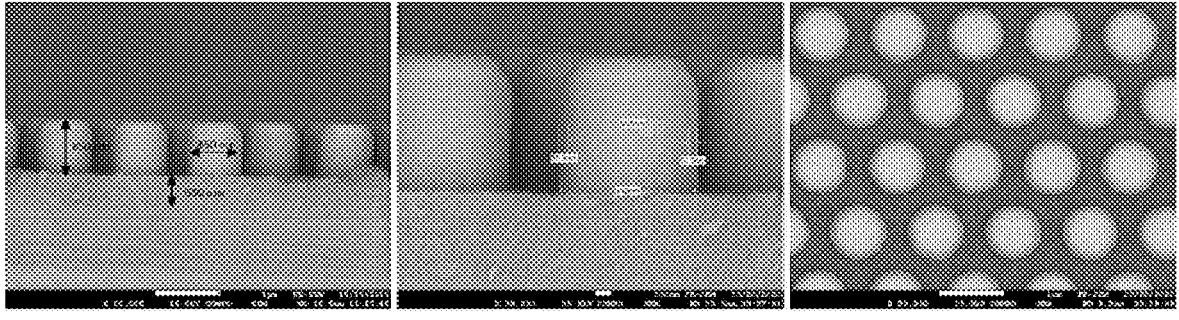

After that, the LED wafer on which a temporary protective film was formed was immersed in an electrolyte, which was an aqueous 0.3 M oxalic acid solution, and connected to the anode terminal of a power supply, the cathode terminal was connected to the platinum electrode immersed in the electrolyte, and then a 10V voltage was applied for 5 minutes. Accordingly, a number of pores was formed from the surface of the first portion (a) of the doped n-type III-nitride semiconductor layer to a depth of 600 nm, as shown in the SEM photograph in FIG. 24. After removing the temporary protective film through ME, a surface protective film made of $Al_2O_3$ was re-deposited on the LED wafer with a thickness of 50 nm based on the side surface of the LED structure. The surface protective film formed on the upper surface of the plurality of LED structures and the surface protective film formed on the surface ($S_1$) of the first portion (a) of the doped n-type III-nitride semiconductor layer were removed by ICP to expose the upper surface ($S_1$) of the first portion (a) of the doped n-type III-nitride semiconductor layer and the upper surface of the LED structure.

Figure 25:
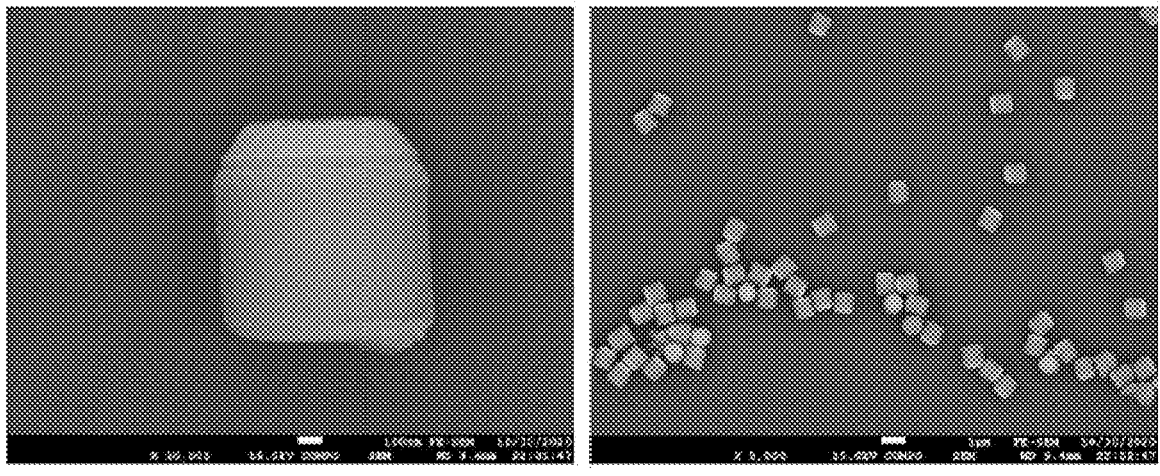
FIG. 25 is an SEM photograph of an ultra-thin LED device (type 1) used in an embodiment of the present invention.
Figure 26:
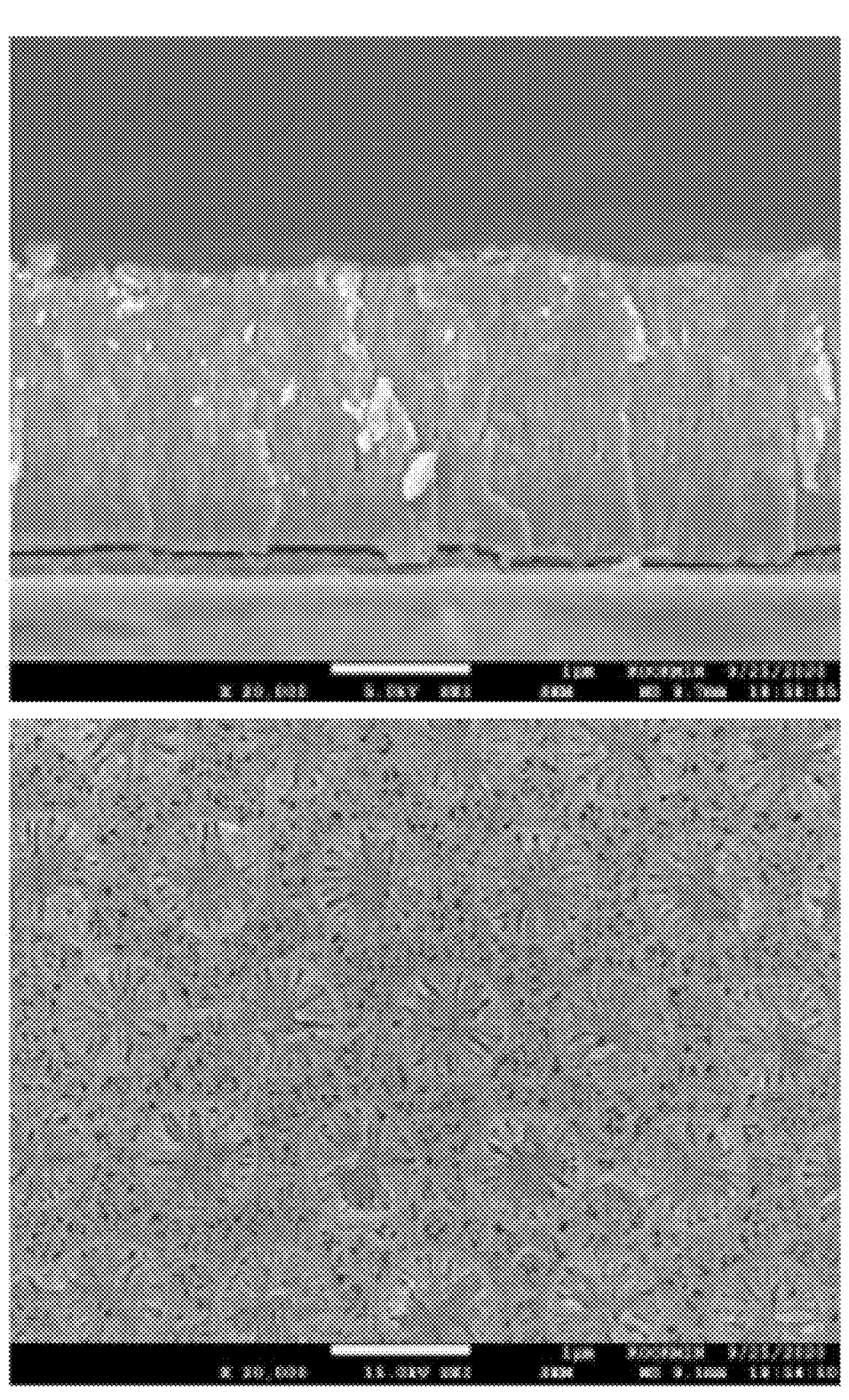
FIG. 26 is an SEM photograph of an LED wafer remained after manufacturing an ultra-thin LED device in a manufacturing process of an ultra-thin LED device (type 1) used in an embodiment of the present invention.

Thereafter, the LED wafer was immersed in a form forming solution of gamma-butyllactone and then irradiated with ultrasonic waves at a frequency of 40 kHz for 10 minutes. Then, by using the generated foams to collapse the pores formed in the doped n-type III-nitride semiconductor layer, a plurality of LED structures was separated from the wafer as shown in the SEM photograph in FIG. 25. As a result, an ultra-thin LED device assembly including the ultra-thin LED devices was manufactured. Also, as shown in FIG. 26, it was confirmed that there was no non-separated LED structure on the wafer.

Comparative Preparation Example 1: Rod Type LED Device

A rod-type LED device assembly having the same stacked structure as in Example 1 having a diameter of 650 nm and a height of 4.2 μm was manufactured from an LED wafer through a conventional method.

Experimental Example 1

After each of the LED device assembly prepared in Preparation Example 1 and Comparative Preparation Example 1 was put into acetone and dispersed by irradiating ultrasonic waves under 100 W condition, the dispersion state of the LED device was measured and confirmed by absorbance for 2 hours at 15-minute intervals. The spectral area of the visible light region of 380 to 780 nm was normalized using the measured results, and the absorbance graph for each time was shown in FIG. 27.

Figure 27:
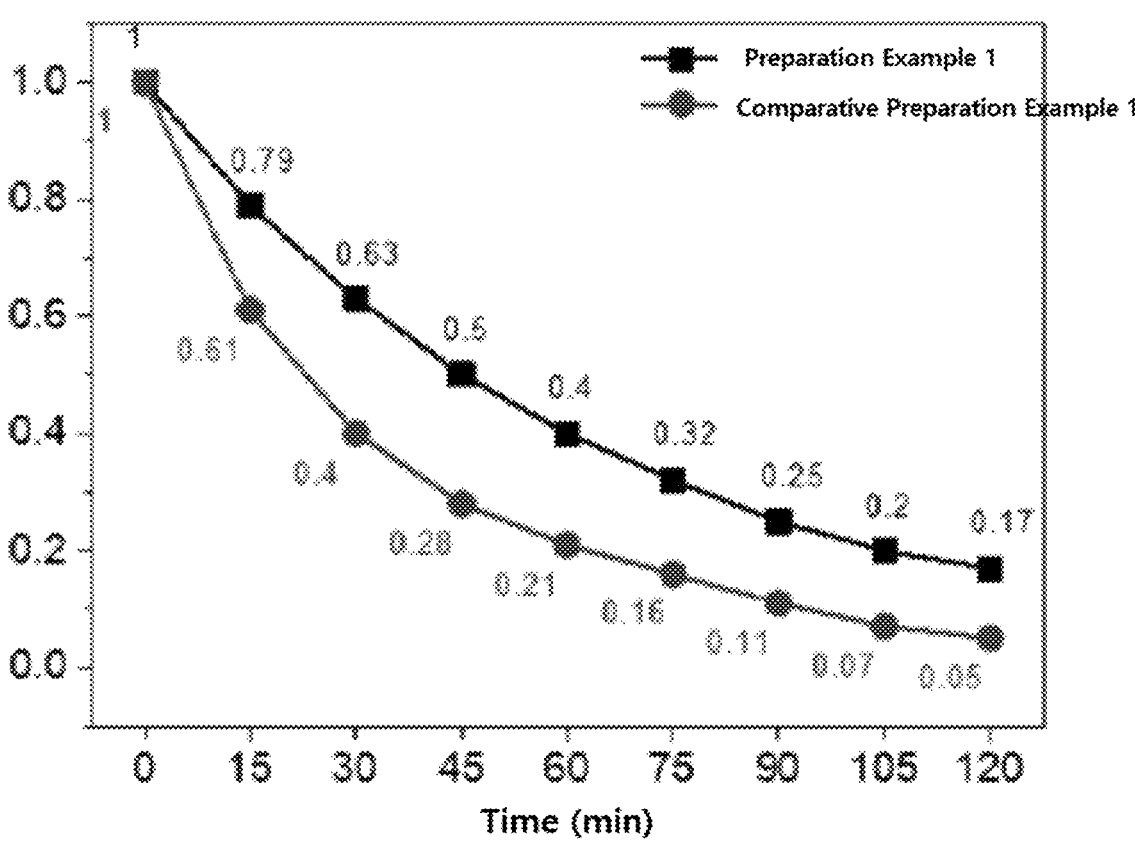
FIG. 27 is an absorbance graph for each time in which the spectral area of the visible light area of 380 to 780 nm is normalized using the absorbance for each wavelength measured over time in an ink composition in which an ultra-thin LED device (type 1) and a rod-type LED device are dispersed in acetone, respectively.

As can be seen from FIG. 27, it can be seen that the ultra-thin LED device according to Preparation Example 1 has excellent dispersion retention in acetone solvent for a long time compared to the rod-type LED device according to Comparative Preparation Example 1.

Example 1: Preparation of Ultra-Thin LED Electrode Assembly

The ultra-thin LED device was prepared in the same manner as that prepared in Preparation Example 1, but before separating from the LED wafer through ultrasonic waves, a Ti/Au layer (thickness of 10 nm/100 nm) was further formed as an electrode layer on the lower electrode layer, and then 1,2-ethanedithiol was treated on the Ti/Au layer to form a binding layer in which the thiol group was exposed.

Thereafter, the lower electrode line including the lower electrode was immersed in the ink composition containing the ultra-thin LED device assembly, and the ultra-thin LED device was erected on the lower electrode for a certain period of time and assembled. The ultra-thin LED device used in this case had a diameter of 750 nm and a height of 1.1 μm. After forming $SiO_2$ as an insulating layer to act as an insulator in a thickness of 1.4 μm to 1.6 μm, in order to expose 300 nm to 400 nm of n-GaN of the ultra-thin LED device, the formed insulating layer was etched by the corresponding thickness. Then, 150 nm of Azo or ITO used as a transparent electrode was deposited on the exposed ultra-thin LED device to form an upper electrode line including an upper electrode on the ultra-thin LED device. As a result, an ultra-thin LED electrode assembly measuring 0.3 mm in width and length, respectively, was manufactured.

Experimental Example 2

Power was applied to the upper electrode line and the lower electrode line of the ultra-thin LED electrode assembly prepared in Example 1, and a light-emitting ultra-thin LED electrode assembly was manufactured.

The ultra-thin LED device applied to the flexible LED skin patch of the present invention and the LED electrode assembly using the same are advantageous in achieving high luminance and luminous efficiency by increasing the emitting area of the device compared to the electrode assembly using the conventional rod-type LED device. In addition, while increasing the emitting area of the device, the area of the photoactive layer exposed on the surface is greatly reduced to prevent or minimize the decrease in efficiency due to surface defects, so that it is possible to implement an electrode assembly having excellent quality. Furthermore, the used LED device minimizes the decrease in electron-hole recombination efficiency due to non-uniformity of electron and hole velocities and the reduction in luminous efficiency due to this, and is very suitable for a method of self-aligning the device on the electrode by an electric field. Therefore, it is possible to more easily implement the electrode assembly. Still further, the flexible LED skin patch of the present invention using an ultra-thin LED device having a specific emission wavelength range, among these ultra-thin LED devices, can be thinned compared to the conventional skin-adhesive skin patch and has excellent luminous efficiency. Thus, it is possible to provide a flexible skin patch that has excellent vitamin D production promoting effect in localized areas of the skin, and has effect of alleviating or treating local skin psoriasis, fungi, fungal tumors and eczema, has excellent antiviral effect, and is easy to attach and detach.

Although a preferred embodiment of the present invention has been described above, it is clear that the present invention can use various changes, modifications and equivalents, and can be equally applied by appropriately modifying the above embodiments. Accordingly, the above description is not intended to limit the scope of the present invention, which is defined by the limits of the following claims.

DESCRIPTION OF REFERENCE NUMERALS

10: first conductive semiconductor layer
20: photoactive layer
30: second conductive semiconductor layer
40: lower electrode layer
60: upper electrode layer
80: protective film
90: polarization inducing layer
91: first polarization inducing layer
92: second polarization inducing layer
100,101,103,104,105,106,107: ultra-thin LED device
200, 310: lower electrode line
211, 212, 213, 214, 311,312: lower electrode(or first electrode)
300, 320: upper electrode line
301, 302, 321,322: upper electrode (or second electrode)
400: substrate
500: conducting metal layer
600: insulating layer
1000, 1001: ultra-thin LED electrode assembly

What is claimed is:

1. A flexible ultra-thin LED skin patch, comprising:
an LED electrode assembly comprising an ultra-thin LED device in which
a first conductive semiconductor layer that is an n-type III-nitride semiconductor layer,
a photoactive layer, and
a second conductive semiconductor layer that is a p-type III-nitride semiconductor layer are stacked,
wherein on side surfaces of the stacked layers,
a hole pushing film that surrounds a side surface so as to directly contact a surface of the second conductive semiconductor layer to move holes on a surface side toward a center, and
an electron pushing film that surrounds a side surface so as to directly contact a surface of the first conductive semiconductor layer to move electrons on a surface side toward the center are provided,
wherein a maximum surface area, which is a maximum value of surfaces during projection, is 4.0 μm2 or less,
wherein the ultra-thin LED device includes an LED device that emits UV of a wavelength of 280 to 400 nm, and the ultra-thin LED device includes at least one selected from:

a dot type LED device, wherein the dot type LED device comprises a thickness in a stacking direction of the layers of 2,000 nm or less and a ratio between the thickness and a length of a long axis in a cross-section perpendicular to the stacking direction of 1:0.5 to 1.5, a disk type LED device, wherein the disk type LED device comprises a thickness in a stacking direction of the layers of 2,000 nm or less and a ratio of 1:1.5 to 5.0, and a micro-nanofin LED device, wherein the micro-nanofin LED device comprises a thickness in a stacking direction of 100 to 3,000 nm and a length of a long axis in a vertical cross-section of 100 to 10,000 nm and has a ratio between the thickness and the length of the long axis of 1:3.

2. The flexible ultra-thin LED skin patch according to claim 1, wherein the LED electrode assembly includes: a lower electrode line including a single or a plurality of lower electrodes; a plurality of the ultra-thin LED devices that is erected and disposed on the lower electrode in the stacking direction of the layers; and an upper electrode line including a single or a plurality of upper electrodes disposed on the plurality of ultra-thin LED devices.

3. The flexible ultra-thin LED skin patch according to claim 2, further comprising an arrangement inducing layer that erects and disposes the ultra-thin LED device in a thickness direction on one side of the ultra-thin LED device in the thickness direction and either one or both sides of a disposing area in which the ultra-thin LED device is to be disposed, wherein the arrangement inducing layer is a magnetic layer, a charge layer or a binding layer.

4. The flexible ultra-thin LED skin patch according to claim 1, wherein the first conductive semiconductor layer of the ultra-thin LED device is an n-type III-nitride semiconductor layer, wherein the flexible ultra-thin LED skin patch further comprises an electron delay layer on a surface opposite to one surface of the first conductive semiconductor layer adjacent to the photoactive layer so that a number of recombination electrons and a number of recombination holes in the photoactive layer are balanced.

5. The flexible ultra-thin LED skin patch according to claim 4, wherein the first conductive semiconductor layer is a doped n-type III-nitride semiconductor layer, the electron delay layer is a III-nitride semiconductor having a doping concentration lower than that of the first conductive semiconductor layer.

6. The flexible ultra-thin LED skin patch according to claim 1, wherein the second conductive semiconductor layer of the ultra-thin LED device is a p-type III-nitride semiconductor layer, wherein the flexible ultra-thin LED skin patch further comprises an electron delay layer on a surface opposite to one surface of the second conductive semiconductor layer adjacent to the photoactive layer so that a number of recombination electrons and a number of recombination holes in the photoactive layer are balanced.

7. The flexible ultra-thin LED skin patch according to claim 4, wherein the electron delay layer includes at least one selected from CdS, GaS, ZnS, CdSe, CaSe, ZnSe, CdTe, GaTe, SiC, ZnO, ZnMgO, SnO2, TiO2, In2O3, Ga2O3, Si, poly (para-phenylene vinylene) and derivatives thereof, polyaniline, poly(3-alkylthiophene) and poly (paraphenylene).

8. The flexible ultra-thin LED skin patch according to claim 1, wherein the ultra-thin LED device includes both the hole pushing film and the electron pushing film, and the electron pushing film is provided as an outermost film surrounding the side surfaces of the first conductive semiconductor layer, photoactive layer, and second conductive semiconductor layer.

9. The flexible ultra-thin LED skin patch according to claim 1, wherein the hole pushing film includes at least one selected from AlNx, ZrO2, MoO, Sc2O3, La2O3, MgO, Y2O3, Al2O3, Ga2O3, TiO2, ZnS, Ta2Os and n-MoS2.

10. The flexible ultra-thin LED skin patch according to claim 1, wherein the electron pushing film includes at least one selected from Al2O3, HfO2, SiNx, SiO2, ZrO2, Sc2O3, AlNx and Ga2O3.

11. The flexible ultra-thin LED skin patch according to claim 2, wherein when the ultra-thin LED device is the micro-nanofin LED device, the micro-nanofin LED device further includes a polarization inducing layer stacked on an upper portion of the second conductive semiconductor layer.

12. The flexible ultra-thin LED skin patch according to claim 2, wherein when the ultra-thin LED device is the micro-nanofin LED device, the first conductive semiconductor layer or polarization inducing layer of the micro-nanofin LED device is disposed so as to be in contact with at least two adjacent lower electrodes.

13. The flexible ultra-thin LED skin patch according to claim 1, wherein the ultra-thin LED device includes at least one selected from the LED device emitting UVC of the wavelength of 200 to 280 nm, the LED device emitting UVB of the wavelength of 280 to 320 nm, and the LED device emitting UVA of the wavelength of 221 to 400 nm.

14. The flexible ultra-thin LED skin patch according to claim 1, wherein the LED electrode assembly is formed on a flexible substrate.

15. The flexible ultra-thin LED skin patch according to claim 1, further comprising: a substrate including a skin adhesive layer including an adhesive pad or an adhesive film; and the LED electrode assembly provided on the substrate, wherein the substrate is transparent.

16. The flexible ultra-thin LED skin patch according to claim 2, wherein the LED electrode assembly is encapsulated with an encapsulant, and each of the lower electrode and the upper electrode is a flexible electrode.

17. The flexible ultra-thin LED skin patch according to claim 1, wherein the flexible ultra-thin LED skin patch promotes a production of vitamin D in a skin.

18. The flexible ultra-thin LED skin patch according to claim 1, wherein the flexible ultra-thin LED skin patch alleviates skin disease or improves skin condition.

19. A method for manufacturing a flexible ultra-thin LED skin patch manufactured by combining the LED electrode assembly according to claim 1 with a substrate including a skin adhesive layer.

* * * * *